(12) United States Patent
Ignagni et al.

(10) Patent No.: US 7,962,215 B2
(45) Date of Patent: Jun. 14, 2011

(54) VENTILATORY ASSIST SYSTEM AND METHODS TO IMPROVE RESPIRATORY FUNCTION

(75) Inventors: Anthony R. Ignagni, Oberlin, OH (US); Raymond P. Onders, Shaker Heights, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 700 days.

(21) Appl. No.: 11/716,459

(22) Filed: Mar. 9, 2007

(65) Prior Publication Data

US 2007/0265611 A1 Nov. 15, 2007

Related U.S. Application Data

(63) Continuation-in-part of application No. 10/897,685, filed on Jul. 23, 2004, now Pat. No. 7,840,270.

(60) Provisional application No. 60/767,201, filed on Mar. 9, 2006, provisional application No. 60/861,568, filed on Nov. 28, 2006, provisional application No. 60/872,265, filed on Dec. 1, 2006.

(51) Int. Cl.
*A61N 1/36* (2006.01)

(52) U.S. Cl. ........................................ 607/42

(58) Field of Classification Search ................ 607/116
See application file for complete search history.

(56) References Cited

U.S. PATENT DOCUMENTS

| | | | |
|---|---|---|---|
| 1,693,734 A | 12/1928 | Waggoner | |
| 2,532,788 A | 12/1950 | Sarnoff | |
| 2,664,880 A | 1/1954 | Wales, Jr. | |
| 4,699,875 A | 10/1987 | Appel | |
| 4,827,935 A | 5/1989 | Geddes et al. | |
| 4,830,008 A | 5/1989 | Meer | |
| 4,989,617 A | 2/1991 | Memberg et al. | |

(Continued)

FOREIGN PATENT DOCUMENTS

EP 996482 A1 5/2000

(Continued)

OTHER PUBLICATIONS

Onders et al.; U.S. Appl. No. 12/122,482 entitled "Devices and methods for assessing motor point electromyogram as a biomarker," filed May 16, 2008.

(Continued)

*Primary Examiner* — Carl H Layno
*Assistant Examiner* — Jeremiah T Kimball
(74) *Attorney, Agent, or Firm* — Shay Glenn LLP

(57) ABSTRACT

Systems and methods are provided to improve respiratory function. Systems include an external electrical stimulator coupled to electrodes that stimulates diaphragm contraction and may optionally include a positive pressure mechanical ventilator. The system further includes an electrode suitable for temporary implantation. Electrical stimulation is provided to specific portions of the diaphragm, such as one hemidiaphragm preferentially over another. By preferentially contracting one hemidiaphragm, a specific portion of a lung may be expanded, such as a posterior portion. By the provision of the negative intrathoracic pressure from diaphragm contraction, greater expansion of specific portion of lung is achieved in relationship to air pressure within the lung, thereby improving compliance. Supplementation of stimulated diaphragm contraction with positive pressure driven air flow from a PPMV directs the air flow to specific portions of the lung. Such portion may include a posterior portion of a lung, and may cause a clearing of atelectasis in that portion.

16 Claims, 14 Drawing Sheets

U.S. PATENT DOCUMENTS

| | | | |
|---|---|---|---|
| 5,056,519 | A | 10/1991 | Vince |
| 5,314,463 | A * | 5/1994 | Camps et al. ................ 607/129 |
| 5,368,035 | A * | 11/1994 | Hamm et al. ................ 600/466 |
| 5,429,636 | A | 7/1995 | Shikhman et al. |
| 5,472,438 | A | 12/1995 | Schmit et al. |
| 5,524,632 | A | 6/1996 | Stein et al. |
| 5,527,358 | A * | 6/1996 | Mehmanesh et al. ......... 607/129 |
| 5,678,535 | A | 10/1997 | DiMarco |
| 5,716,392 | A | 2/1998 | Bourgeois et al. |
| 5,718,248 | A | 2/1998 | Trumble et al. |
| 5,792,165 | A | 8/1998 | Klieman et al. |
| 5,797,923 | A | 8/1998 | Aiyar et al. |
| 5,813,399 | A | 9/1998 | Isaza et al. |
| 5,814,086 | A | 9/1998 | Hirschberg et al. |
| 5,849,290 | A | 12/1998 | Brown et al. |
| 5,851,783 | A | 12/1998 | Appel et al. |
| 6,035,856 | A | 3/2000 | LaFontaine et al. |
| 6,194,217 | B1 | 2/2001 | Matson |
| 6,198,970 | B1 | 3/2001 | Freed et al. |
| 6,210,970 | B1 | 4/2001 | Matson |
| 6,245,053 | B1 * | 6/2001 | Benjamin ................ 604/523 |
| 6,254,425 | B1 | 7/2001 | Shchervinsky et al. |
| 6,311,692 | B1 | 11/2001 | Vaska et al. |
| 6,321,109 | B2 | 11/2001 | Ben-Haim et al. |
| 6,360,740 | B1 | 3/2002 | Ward et al. |
| 6,397,108 | B1 | 5/2002 | Camps et al. |
| 6,405,732 | B1 | 6/2002 | Edwards et al. |
| 6,415,183 | B1 | 7/2002 | Scheiner et al. |
| 6,463,327 | B1 | 10/2002 | Lurie et al. |
| 6,477,423 | B1 | 11/2002 | Jenkins |
| 6,571,127 | B1 | 5/2003 | Ben-Haim et al. |
| 6,645,145 | B1 | 11/2003 | Dreschel et al. |
| 6,845,271 | B2 * | 1/2005 | Fang et al. ................ 607/74 |
| 6,918,871 | B2 | 7/2005 | Schulze |
| 6,947,792 | B2 | 9/2005 | Ben-Haim et al. |
| 7,006,871 | B1 | 2/2006 | Darvish et al. |
| 7,044,921 | B2 | 5/2006 | Asmus et al. |
| 7,071,194 | B2 | 7/2006 | Teng |
| 7,107,092 | B2 | 9/2006 | Goldstein et al. |
| 7,120,497 | B2 | 10/2006 | Ben-Haim et al. |
| 7,155,278 | B2 | 12/2006 | King et al. |
| 7,165,551 | B2 | 1/2007 | Edwards et al. |
| 7,195,881 | B2 | 3/2007 | Geffard |
| 7,206,636 | B1 | 4/2007 | Turcott |
| 7,207,946 | B2 | 4/2007 | Sirokman |
| 7,221,978 | B2 | 5/2007 | Ben-Haim et al. |
| 7,225,016 | B1 | 5/2007 | Koh |
| 7,329,489 | B2 | 2/2008 | Kaddurah-Daouk et al. |
| 7,356,521 | B2 | 4/2008 | Wang et al. |
| 7,418,298 | B2 * | 8/2008 | Shiroff et al. ................ 607/126 |
| 7,463,934 | B2 * | 12/2008 | Tronnes et al. ............... 607/133 |
| 7,840,270 | B2 * | 11/2010 | Ignagni et al. .................. 607/42 |
| 2001/0025177 | A1 | 9/2001 | Woloszko et al. |
| 2001/0049497 | A1 | 12/2001 | Kalloo et al. |
| 2002/0103424 | A1 | 8/2002 | Swoyer et al. |
| 2003/0040785 | A1 | 2/2003 | Maschino et al. |
| 2003/0148404 | A1 | 8/2003 | Michaelson |
| 2003/0171672 | A1 | 9/2003 | Varghese et al. |
| 2003/0175832 | A1 | 9/2003 | Marton et al. |
| 2004/0003813 | A1 | 1/2004 | Banner et al. |
| 2004/0044377 | A1 | 3/2004 | Larsson |
| 2004/0064069 | A1 | 4/2004 | Reynolds et al. |
| 2004/0122360 | A1 * | 6/2004 | Waldhauser et al. ....... 604/95.04 |
| 2004/0167437 | A1 | 8/2004 | Sharrow et al. |
| 2004/0167442 | A1 | 8/2004 | Shireman et al. |
| 2004/0167443 | A1 | 8/2004 | Shireman et al. |
| 2004/0172090 | A1 | 9/2004 | Janzig et al. |
| 2004/0177388 | A1 | 9/2004 | Botas et al. |
| 2004/0254572 | A1 | 12/2004 | McIntyre et al. |
| 2004/0260198 | A1 | 12/2004 | Rothberg et al. |
| 2004/0260245 | A1 | 12/2004 | Clem et al. |
| 2004/0260246 | A1 | 12/2004 | Desmond |
| 2004/0260337 | A1 | 12/2004 | Freed |
| 2005/0021102 | A1 | 1/2005 | Ignagni et al. |
| 2005/0033394 | A1 | 2/2005 | Seifert et al. |
| 2005/0049523 | A1 | 3/2005 | Crank |
| 2005/0054950 | A1 | 3/2005 | Parins |
| 2005/0054951 | A1 | 3/2005 | Parins |
| 2005/0054952 | A1 | 3/2005 | Eskuri et al. |
| 2005/0080463 | A1 | 4/2005 | Stahmann et al. |
| 2005/0085734 | A1 | 4/2005 | Tehrani |
| 2005/0085865 | A1 | 4/2005 | Tehrani |
| 2005/0085866 | A1 | 4/2005 | Tehrani |
| 2005/0085867 | A1 | 4/2005 | Tehrani et al. |
| 2005/0085868 | A1 | 4/2005 | Tehrani et al. |
| 2005/0085869 | A1 | 4/2005 | Tehrani et al. |
| 2005/0107781 | A1 | 5/2005 | Ostrovsky et al. |
| 2005/0107812 | A1 | 5/2005 | Starksen et al. |
| 2005/0107860 | A1 | 5/2005 | Ignagni et al. |
| 2005/0109340 | A1 | 5/2005 | Tehrani |
| 2005/0113710 | A1 | 5/2005 | Stahmann et al. |
| 2005/0115561 | A1 | 6/2005 | Stahmann et al. |
| 2005/0124917 | A1 | 6/2005 | Skujins et al. |
| 2005/0137501 | A1 | 6/2005 | Euteneuer et al. |
| 2005/0148026 | A1 | 7/2005 | Bowser et al. |
| 2005/0148818 | A1 | 7/2005 | Mesallum |
| 2005/0165457 | A1 | 7/2005 | Benser et al. |
| 2005/0209653 | A1 | 9/2005 | Herbert et al. |
| 2005/0240241 | A1 | 10/2005 | Yun et al. |
| 2005/0277945 | A1 | 12/2005 | Saadat et al. |
| 2006/0030894 | A1 | 2/2006 | Tehrani |
| 2006/0035849 | A1 | 2/2006 | Spiegelman et al. |
| 2006/0036294 | A1 | 2/2006 | Tehrani |
| 2006/0041022 | A1 | 2/2006 | Pasinetti |
| 2006/0068452 | A1 | 3/2006 | Goldknopf et al. |
| 2006/0088862 | A1 | 4/2006 | Lee |
| 2006/0115854 | A1 | 6/2006 | Goldknopf et al. |
| 2006/0115855 | A1 | 6/2006 | Goldknopf et al. |
| 2006/0115856 | A1 | 6/2006 | Goldknopf et al. |
| 2006/0115867 | A1 | 6/2006 | Goldknopf et al. |
| 2006/0121619 | A1 | 6/2006 | Bowser |
| 2006/0122662 | A1 | 6/2006 | Tehrani et al. |
| 2006/0130161 | A1 | 6/2006 | Genain |
| 2006/0130833 | A1 | 6/2006 | Younes |
| 2006/0142815 | A1 | 6/2006 | Tehrani et al. |
| 2006/0149316 | A1 | 7/2006 | DeVries et al. |
| 2006/0149334 | A1 | 7/2006 | Tehrani et al. |
| 2006/0155222 | A1 | 7/2006 | Sherman et al. |
| 2006/0155341 | A1 | 7/2006 | Tehrani et al. |
| 2006/0160087 | A1 | 7/2006 | McGrath et al. |
| 2006/0167523 | A1 | 7/2006 | Tehrani et al. |
| 2006/0224209 | A1 | 10/2006 | Meyer |
| 2006/0247729 | A1 | 11/2006 | Tehrani et al. |
| 2006/0258667 | A1 | 11/2006 | Teng |
| 2006/0281809 | A1 | 12/2006 | Miller et al. |
| 2006/0282131 | A1 | 12/2006 | Caparso et al. |
| 2006/0286167 | A1 | 12/2006 | Staunton et al. |
| 2006/0287679 | A1 | 12/2006 | Stone |
| 2007/0017809 | A1 | 1/2007 | Goldknopf et al. |
| 2007/0021421 | A1 | 1/2007 | Hampton |
| 2007/0021500 | A1 | 1/2007 | Twyman et al. |
| 2007/0021795 | A1 | 1/2007 | Tehrani |
| 2007/0038127 | A1 | 2/2007 | Goldstein et al. |
| 2007/0049793 | A1 | 3/2007 | Ignagni et al. |
| 2007/0054852 | A1 | 3/2007 | Lin et al. |
| 2007/0072943 | A1 | 3/2007 | Miller et al. |
| 2007/0078099 | A1 | 4/2007 | McLaurin |
| 2007/0087000 | A1 | 4/2007 | Walsh et al. |
| 2007/0087314 | A1 | 4/2007 | Gomo |
| 2007/0098812 | A1 | 5/2007 | Feinstein et al. |
| 2007/0117772 | A1 | 5/2007 | Bennett et al. |
| 2007/0118183 | A1 | 5/2007 | Gelfand et al. |
| 2007/0122813 | A1 | 5/2007 | Salomon et al. |
| 2007/0150006 | A1 | 6/2007 | Libbus et al. |
| 2007/0150023 | A1 | 6/2007 | Ignagni et al. |
| 2007/0172820 | A1 | 7/2007 | Kaddurah-Daouk et al. |
| 2007/0191908 | A1 | 8/2007 | Jacob et al. |
| 2007/0196780 | A1 | 8/2007 | Ware et al. |
| 2007/0197932 | A1 | 8/2007 | Feke et al. |
| 2007/0202515 | A1 | 8/2007 | Hadlock et al. |
| 2007/0202537 | A1 | 8/2007 | Lingappa et al. |
| 2007/0221224 | A1 | 9/2007 | Pittman et al. |
| 2007/0225261 | A1 | 9/2007 | Miller et al. |
| 2007/0240718 | A1 | 10/2007 | Daly |
| 2007/0250162 | A1 | 10/2007 | Royalty |
| 2007/0274992 | A1 | 11/2007 | Michalovich et al. |
| 2007/0282388 | A1 | 12/2007 | Sandyk |

| | | | |
|---|---|---|---|
| 2007/0292403 | A1 | 12/2007 | Nivaggioli |
| 2007/0292410 | A1 | 12/2007 | Cashman et al. |
| 2007/0298998 | A1 | 12/2007 | Paige et al. |
| 2008/0003208 | A1 | 1/2008 | Nivaggioli |

FOREIGN PATENT DOCUMENTS

| | | | |
|---|---|---|---|
| EP | 873155 B1 | 6/2003 | |
| EP | 1634617 A1 | 3/2006 | |
| EP | 1653863 A2 | 5/2006 | |
| EP | 1658020 A1 | 5/2006 | |
| EP | 1660177 A1 | 5/2006 | |
| EP | 1663370 A2 | 6/2006 | |
| EP | 1667757 A2 | 6/2006 | |
| EP | 1670611 A2 | 6/2006 | |
| EP | 1684655 A2 | 8/2006 | |
| EP | 1393773 B1 | 10/2006 | |
| EP | 1306104 B1 | 1/2007 | |
| EP | 1205202 B1 | 6/2007 | |
| WO | WO 86/00234 A1 | 1/1986 | |
| WO | WO 2005/039691 A1 | 5/2005 | |
| WO | WO 2006/062710 A1 | 6/2006 | |
| WO | WO 2006/079152 A1 | 8/2006 | |
| WO | WO 2006/083675 A2 | 8/2006 | |
| WO | WO 2006/088696 A2 | 8/2006 | |
| WO | WO 2006/121447 A2 | 11/2006 | |
| WO | WO 2006/124023 A1 | 11/2006 | |
| WO | WO 2006/131150 A1 | 12/2006 | |
| WO | WO 2006/138069 A1 | 12/2006 | |
| WO | WO 2007/035804 A2 | 3/2007 | |
| WO | WO 2007/053230 A2 | 5/2007 | |
| WO | WO 2007/058780 A2 | 5/2007 | |
| WO | WO 2007/058938 A2 | 5/2007 | |
| WO | WO 2007/061902 A2 | 5/2007 | |
| WO | WO 2007/082384 A1 | 7/2007 | |
| WO | WO 2007/103585 A2 | 9/2007 | |
| WO | WO 2007/109443 A2 | 9/2007 | |
| WO | WO 2007/128002 A2 | 11/2007 | |

OTHER PUBLICATIONS

DeCarvalo et al.; Motor neuron disease presenting with respiratory failure; Journal of the Neurological Sciences; vol. 139; no. Suppl.; 1996; pp. 117-122.

Stewart et al.; Electromyography of respiratory muscles in amyotrophic lateral sclerosis; Journal of the Neurological Sciences; vol. 191; No. 1-2; Oct. 15, 2001; pp. 67-73.

Ignagni et al.; U.S. Appl. No. 12/261,979 entitled "Method of improving sleep disordered breathing," filed Oct. 30, 2008.

Ayas et al; Prevention of human diaphragm atrophy with short periods of electrical stimulation; Am J Respir Crit Care Med; vol. 159; pp. 2018-2020; 1999.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147; 273-287; 2005.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Nochomovitz et al.; Conditioning of the diaphragm with phrenic nerve stimulation after prolonged disuse; American Review of Respiratory Disease; vol. 130; No. 4; 325-329; Oct. 1984.

Nochomovitz et al.; Diaphragm activation with intramuscular stimulation in dogs; American Review of Respiratory Disease; vol. 127; No. 3; 685-687; Mar. 1983.

Onders et al.; Early results of laparoscopic motor point diaphragm pacing in amyotrophic lateral sclerosis; Amyotrophic Lateral Sclerosis (Abstracts from the 16th Intl. Symp. ALS/MND; vol. 6, supp. 1; ISSN1743-4475; pp. 142-143; Dec. 2005.

Onders et al.; Mapping the phrenic nerve motor point: the key to a successful laparoscopic diaphragm pacing system in the first human series; Surgery; vol. 136; No. 4; 819-26; Oct. 2004.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Ignagni et al; U.S. Appl. No. 11/716,475 entitled "Ventilatory assist system and methods to improve respiratory function," filed Mar. 9, 2007.

Ignagni et al; U.S. Appl. No. 11/467,025 entitled "Method and apparatus for grasping an abdominal wall," filed Aug. 24, 2006.

Ignagni et al; U.S. Appl. No. 12/026,428 entitled "Intramuscular electrode," filed Feb. 5, 2008.

Ignagni et al.; U.S. Appl. No. 12/904,993 entitled "System and Method for Conditioning a Diaphragm of a Patient," filed Oct. 14, 2010.

Bhadra et al.; Extraction force and tissue change during removal of a tined intramuscular electrode from rat gastrocnemius; Annals of Biomedical Engineering; vol. 34; No. 6; pp. 1042-1050; Jun. 2006.

Ignagni et al.; U.S. Appl. No. 12/690,410 entitled "Device and Method of Neuromodulation to Effect a Functionally Restorative Adaption of the Neuromuscular System," filed Jan. 20, 2010.

Kalloo et al.; Flexible transgastric peritoneoscopy: a novel approach to diagnosis and therapeutic intervention in the peritoneal cavity; Gastrointestinal Endoscopy; vol. 60; No. 1; pp. 114-117; 2004.

Roos et al.; Improved cardiac performance through pacing-induced diaphragmatic stimulation: a novel electrophysiological approach in heart failure management?; Europace; vol. 11; pp. 191-199; 2009.

* cited by examiner

VENTILATORY ASSIST SYSTEM AND METHODS TO IMPROVE RESPIRATORY FUNCTION

REFERENCE TO RELATED APPLICATIONS

This application claims priority to U.S. Provisional Patent Applications No. 60/767,201 which was filed on Mar. 9, 2006, No. 60/861,568 which was filed on Nov. 28, 2006, and No. 60/872,265 which was filed on Dec. 1, 2006, all applications by inventors Ignagni and Onders. This application also claims priority as a continuation-in-part of U.S. application Ser. No. 10/897,685, filed on Jul. 23, 2004, now U.S. Pat. No. 7,840,270 and which was published as U.S. Pub. No. US 2005/0021102 on Jan. 27, 2005. All of the aforementioned applications are hereby incorporated by reference.

FIELD OF THE INVENTION

The invention relates to apparatus and methods for supporting pulmonary function of patients in critical care settings.

BACKGROUND OF THE INVENTION

A patient may need respiratory assistance as a result of disease and/or injuries of various kinds. This need for respiratory assistance can be direct, especially when the injury or illness afflicts the patient's respiratory system. In one example, patients in acute respiratory failure may need respiratory assistance. The need for respiratory assistance can also be indirect, for example as during anesthesia. Typically, the extent of respiratory assistance may encompass a range from facilitating spontaneous breathing to total control of breathing.

A mechanical ventilator that moves gas into the lungs of a patient using positive pressure to move air into the lungs may be used to provide respiratory assistance. Although this respiratory assistance may be life saving, long-term use of a mechanical ventilator may not be ideal. For example, long-term mechanical ventilation use may result in weakening of the diaphragm of the patient because of disuse, and use of positive intrathoracic pressures may cause barotrauma, as well as provide inadequate ventilation of the posterior lobes of the lung, thereby possibly contributing to atelectasis, and generally compromising hemodynamics of the patient, which can have further deleterious consequences.

SUMMARY OF THE INVENTION

Embodiments of the invention include a method for supporting the respiration of patients that are typically in a critical care setting. Embodiments of the invention make use of a system that includes an external stimulator and one or more electrodes adapted for implanting at one or more sites in the diaphragm. The external stimulator is configured to stimulate the one or more electrodes independently, the one or more electrodes connected to the external simulator. The method includes implanting the one or more electrodes in the diaphragm of the patient, initiating a breath, and stimulating the diaphragm with the one or more electrodes during a breath to increase tidal volume and/or to decrease maximal lung pressure during the breath, thereby improving respiratory compliance.

Embodiments of the invention include implanting the electrodes, or stimulating the implanted electrodes in such a way as to stimulate a specific portion of the diaphragm. Such a specific portion of the diaphragm may, for example, include the left hemidiaphragm or the right hemidiaphragm, or any particular portion of the left or right hemidiaphragm. Such stimulation of a particular portion of a diaphragm may preferentially direct negative pressure to a particular portion of a patient's lungs, such as the right lung or the left lung. A particular portion of a lung may include the lower or posterior portion of the lung. In some embodiments, a particular portion of a lung may suffer from atelectasis, or collapse. In such embodiments, directing negative pressure to the collapsed portion may cause a decrease in—or clearing of atelectasis.

In some embodiments of the method, the patient initiates, or attempts to initiate a breath, which is then sensed by the system, such that the patient-initiated breath is subsequently supported to completion by the respiratory support system. Embodiments of the method include sensing the electrical activity in the diaphragmatic muscle through the electrodes of the system, which deliver electromyographic data to the system that are informative as to the diaphragmatic activity. Other embodiments of the method include sensing the initiation of a breath with a sensor placed at the airway of the patient; in some embodiments this is a pressure sensor, in other embodiments it is a flow sensor.

In other embodiments, the patient's breath is initiated by the external stimulator by way of stimulating the diaphragm. In such embodiments, the stimulator may provide a baseline breathing rate, in addition to supporting the breath through completion.

In other embodiments, the ventilator initiates the breath and the external stimulator is used to reduce pressures, increase gas delivered, and/or direct gas flow to dependent portions of the lungs. In such embodiments, the stimulator may be synchronized in timing with the ventilator breathing cycle or electronically triggered by the ventilator or gas flow to assist the ventilator at a specific point in the breathing cycle.

Embodiments of the method include the stimulator being able to vary stimulation parameters with regard to any one or more signal parameters including pulse rate, pulse frequency, pulse amplitude, pulse duration, and pulse ramping. The system may vary these parameters individually to each electrode, each electrode independently of others.

Application of the method, beyond broadly improving respiratory complains, may improve specific aspects of lung performance and patient health. The method may, for example, improve any of hemodynamics venous return, cardiac output, alveolar ventilation, type 1 muscle fiber condition. The method may decrease any of atelectasis, third spacing, time required for weaning from the PPMV, length of hospital stay, occurrence of pneumonia. The method may condition Type I muscle fibers, and may stimulate the conversion of Type IIb muscle fibers into Type I muscle fibers.

Some patients are at risk for the development of central hypoventilation syndrome (CHS), in such patients, the method may support a regular breathing rate during sleep. Disturbed sleep can decrease or prevent occurrence of REM sleep, accordingly, uninterrupted sleep as supported by a regular breathing rate may increase the occurrence or duration of REM sleep. Loss of REM sleep is considered a causative factor in intensive care unit (ICU) psychosis. Accordingly, the method may alleviate the severity or development of ICU psychosis.

In some embodiments, the method is applied to acute patients, who are expected to be weaned from the respiratory support system. In other embodiments, the patient has been previously supported by a positive pressure mechanical ventilator (PPMV), or by a combination of electrical diaphragm stimulation, per the presently described invention, and a PPMV. The method includes the support of these patients by the above described system, after the PPMV support has been discontinued.

As provided by embodiments of the invention, the electrodes may be implanted in the diaphragm any of several anatomical approaches and surgical methods. In some embodiments, the electrodes are implanted by insertion through the abdominal cavity, using either laparoscopic techniques or open surgical techniques. In some embodiments, the electrodes are implanted by insertion through the thoracic cavity, using either thoracoscopic techniques or open surgical techniques. In still other embodiments the electrodes are implanted in the diaphragm by way of insertion through natural orifices, using translumenal endoscopic techniques.

In some embodiments of the invention, the system for the method may further include a positive pressure mechanical ventilator (PPMV), the method further comprising ventilating the patient with the PPMV. In some embodiments, the external stimulator and the PPMV are configured such that the external stimulator controls the PPMV, the method further comprising controlling the PPMV. In such embodiments, controlling the PPMV includes controlling operational parameters of PPMV, the parameters including any of breath rate, gas volume delivered per breath, or airway pressure behind delivered gas. In other embodiments, the external stimulator and the PPMV are configured such that the PPMV controls the external stimulator, the method further comprising controlling the external stimulator. In such embodiments, controlling the external stimulator includes triggering stimulator output at a time in relationship to the PPMV reaching peak pressure. Generally in embodiments that include a PPMV, the method may include controlling the PPMV with a constraint of a maximal tidal volume, or it may include controlling the PPMV with a constraint of a maximal airway pressure In comparing the maximal airway pressure required to deliver a given tidal volume to a patient with a PPMV with and without diaphragmatic stimulation per embodiments of this invention, the airway pressure required by the PPMV is decreased by the concurrent diaphragmatic stimulation. High airway pressure from a PPMV is associated with barotrauma to the lungs of such treated patients, accordingly, inclusion of diaphragm stimulation may reduce the risk of PPMV-associated barotrauma.

Embodiments of the invention also include a method for treating a patient with an atelectatic lung region with a system including an external stimulator and one or more electrodes implanted at one or more sites in the diaphragm, the external stimulator configured to stimulate the one or more electrodes independently, and a positive pressure mechanical ventilator (PPMV). The method includes initiating a breath, ventilating the patient with the PPMV during the breath, stimulating the diaphragm with the one or more electrodes during the breath to increase tidal volume and/or to decrease maximal lung pressure during the breath. The electrodes have been implanted or a stimulated such that they preferentially stimulate a specific portion of the diaphragm such that the volume of atelectatic region is expanded, thereby clearing the atelectatic region.

Embodiments of the invention also include an electrode suitable for temporary placement in tissue that includes a needle at a first end, a central portion including a straight insulated lead, a helically wound insulated lead portion, and a deinsulated coiled portion, and a second end including a deinsulated barb and a stop. In some embodiments, the stop comprises soft silicone. In other embodiments, the stop includes an absorbable suture material thermally bonded to the deinsulated coiled portion. In some embodiments, the needle is a break-away needle. In some embodiments the straight insulated lead and the helically wound insulated lead are joined at a junction, and the electrode further includes a bonding material disposed at the junction to form a bond configured to prevent the helically wound lead from unwinding.

Embodiments of the invention further include a method of inserting an electrode suitable for temporary placement in a tissue site, the electrode including a needle at a first end, a central portion comprising a straight insulated lead, a helically wound insulated lead portion, and a deinsulated coiled portion, and a deinsulated barb and a stop at a second end. The method includes inserting the electrode into a tissue site surface by the first end comprising the needle, and pulling the electrode through the tissue until the second end comprising the stop is at the tissue site surface.

BRIEF DESCRIPTION OF THE DRAWINGS

FIG. 13A shows normal airway pressure waveform with ventilator only. FIG. 13C shows airway pressure with diaphragm stimulation started near beginning of inspiration and lasting for approx. 1 sec-demonstrating an ability to reduce airway pressure and maintain tidal volume. FIG. 13D shows airway pressure with stimulation in first inspiration and no stimulation in second inspiration.

DETAILED DESCRIPTION OF THE INVENTION

System Components

Components of the system for providing respiratory support by the methods described herein include an external stimulator for electrically stimulating a portion of the diaphragm of a patient, electrodes suitable for implanting in the diaphragm, and a positive pressure mechanical ventilator (PPMV). In some embodiments, the system includes only the stimulator and electrodes for respiratory support; other embodiments include the PPMV as well.

External Electrical Stimulator and Implanted Electrodes

Figure 1:
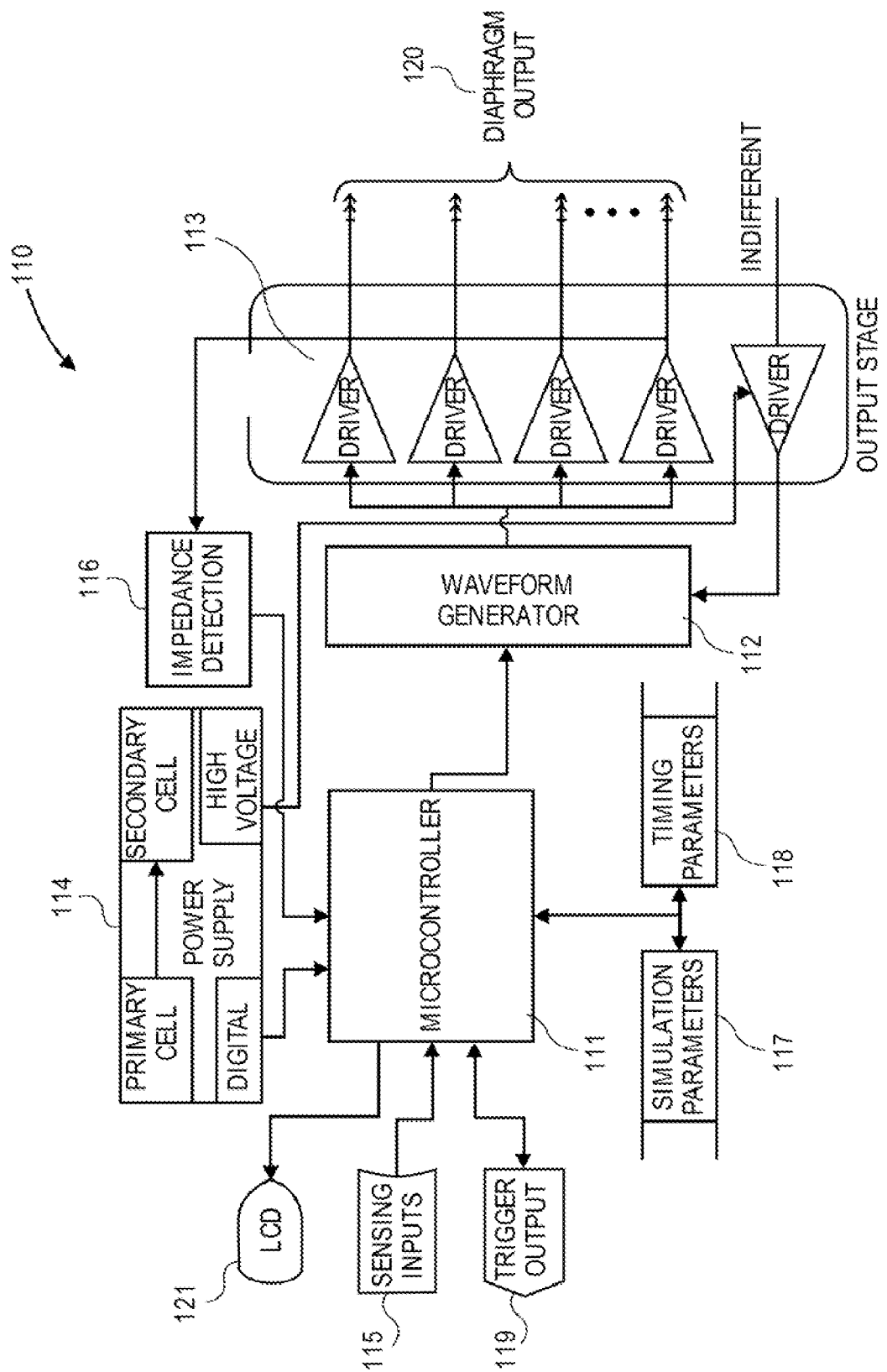
FIG. 1 is a block diagram of the external stimulator.

In one embodiment, the electrical signal generator 110 shown in FIG. 1 can be configured to generate pulses and/or signals that may take the form of sinusoidal, stepped, trapezoidal waveforms or other relatively continuous signals. The electric signal generator 110 can include one or more channels that can independently control the amplitude, frequency, timing and pulse width of the corresponding electrodes connected thereto.

In one embodiment, the electrical signal generator 110 can be an external signal generator that is electrically connected to or in electrical communication with the electrodes. One example of a suitable electrical signal generator is the NeuRx RA/4 stimulator that is manufactured by Synapse Biomedical, Inc. of Oberlin, Ohio. The NeuRx RA/4 stimulator is a four-channel device with independent parameter programmability. It will be appreciated that since the NeuRx RA/4 stimulator has four channels, it has the capability to independently control up to four electrodes. In an alternative embodiment, the electrical signal generator 110 can be an implantable signal generator. One suitable example of a fully implanted signal generator is the "Precision" electrical signal generator available from Boston Scientific/Advanced Bionics. One example of a partially implanted radio-frequency signal generator system is the "XTREL" system available from Medtronic, Inc.

The external stimulator 110 depicted in FIG. 1 is comprised of several blocks to produce coordinated stimulus output. The core of the device is a supervisory microcontroller 111 that coordinates parameter and sensed inputs, display, and stimulus/trigger outputs. The stimulus and timing parameters are stored in non-volatile memory and are programmed, via a serial interface (not shown), specific to the respiratory support needs and electrode muscle recruitment characteristics of the particular patient. The waveform generator 112 assembles the control signals from the microcontroller in the necessary waveform patterns to be output through the output stage signal drivers 113. The microcontroller 111 receives power from a power supply 114. It receives input of sensing information 115, impedance detection 116, stimulation parameters 117 and timing parameters 118. The microcontroller 111 provides output to a trigger output 119 and an LCD 121, in addition to the waveform generator 112. The output stage comprising drivers 113 also provide output to the impedance detector 116. The drivers 113 provide output in the form of stimulation of the electrodes 120.

In the preferred embodiment the resultant output is a capacitively coupled, current regulated biphasic waveform. With each stimulus output the circuit impedance is detected and fed back to the microcontroller to display electrode circuit integrity. The microcontroller may be driven to send the control signals to the waveform generator from an external sensed source (either a digital level or analog signal, such as diaphragm EMG) or from internal timing that is based on the stored timing parameters. The microcontroller may also be programmed to send out an analog or digital trigger signal to an external device based on a programmed sequence or event.

In one example, the electrical signal generator can supply the implantable electrodes with an electrical signal that serves as electrical stimulation to the respiratory system of the patient. For example, the electrical signal can be a capacitively-coupled, charge balanced, biphasic, constant current waveform with adjustable parameters as shown below in Table 1. It will be appreciated that the electrical signal can take the form of other waveforms for electrical stimulation such as monophasic or rectangular biphasic.

TABLE 1

| Parameter | Range |
| --- | --- |
| Stimulation Interleave Rate | 1-100 |
| Trigger Delay (from inspiration) | 1.0-4.0 s |
| Stimulation Time | 0.8-1.5 s |
| Output Pulse Period | 20-250 ms |
| Pulse Width Modulation Count | 0-10 |
| Cathodic Current Amplitude | 5-25 mA |
| Cathodic Current Pulse Width | 20-200 μs |
| Voltage | 0-65 V |
| Pulse Frequency | 10-20 Hz |

Although the stimulatory signal can be delivered to a variety of locations in the body of a patient to stimulate the respiratory system, in one example, the electrical stimulatory can be delivered to the diaphragm of the patient, through the electrodes, continuously or periodically. For example, the electrical stimulation can be delivered to the diaphragm of the patient at specified intervals per day (e.g. 5-6 sessions per day) for a certain period of time per interval (e.g. 5 minutes per session totaling about 25-30 minutes per day). It will be appreciated that the electrical stimulation can be delivered at different intervals depending on the needs of a particular patient.

The external electrical stimulator makes use of one or more intramuscular electrodes that are suitable for implanting into muscle tissue. In some embodiments, the intramuscular electrode can serve as a cathode. In some embodiments, the electrode is particularly adapted for temporary implantation. Features of implantation that provide long term stability, as in a more permanent placement, tend to work against suitability for short-term placement. It is desirable for an electrode to be able to stably remain in the muscle tissue without migrating from the target implant site, and thus supplemental anchoring is generally helpful. However, for an electrode to be appropriate for temporary placement, it needs to be able to be withdrawn intact without significant trauma to the muscle when no longer needed, and supplemental anchoring tends to complicate withdrawal. Similarly, tissue ingrowth, as encouraged by the anchoring or by features of the electrode is desirable for stabilization and protecting the entry site, but such ingrowth can complicate removal. In some instances the electrode may be treated as temporary by just abandoning its use, however that is unsatisfactory as presents risks to the patient of potential migration of unsecured portions, imaging artifact, or thermal/electrochemical effects if exposed to inappropriate MRI or diathermy.

One example of a suitable long-term intramuscular electrode is the Peterson intramuscular electrode (P/N 21-0002) manufactured by Synapse Biomedical, Inc. of Oberlin, Ohio. In one configuration, the Peterson intramuscular electrode is a double helix wound from multistrand stainless steel wire insulated in fluoropolymer with a polypropylene core and barb. The electrode can have a barb that is flattened and bent back along the line of the electrode, a polypropylene skirt, and a deinsulated coil under the skirt. The electrode lead can terminate with a stainless steel pin crimped to the de-insulated end and back-filled with silicone adhesive for strain relief. It will be appreciated that the intramuscular electrode can take the form of other shapes, sizes, and configurations, and can be made of other materials suitable for implantation into a patient.

Figure 2:
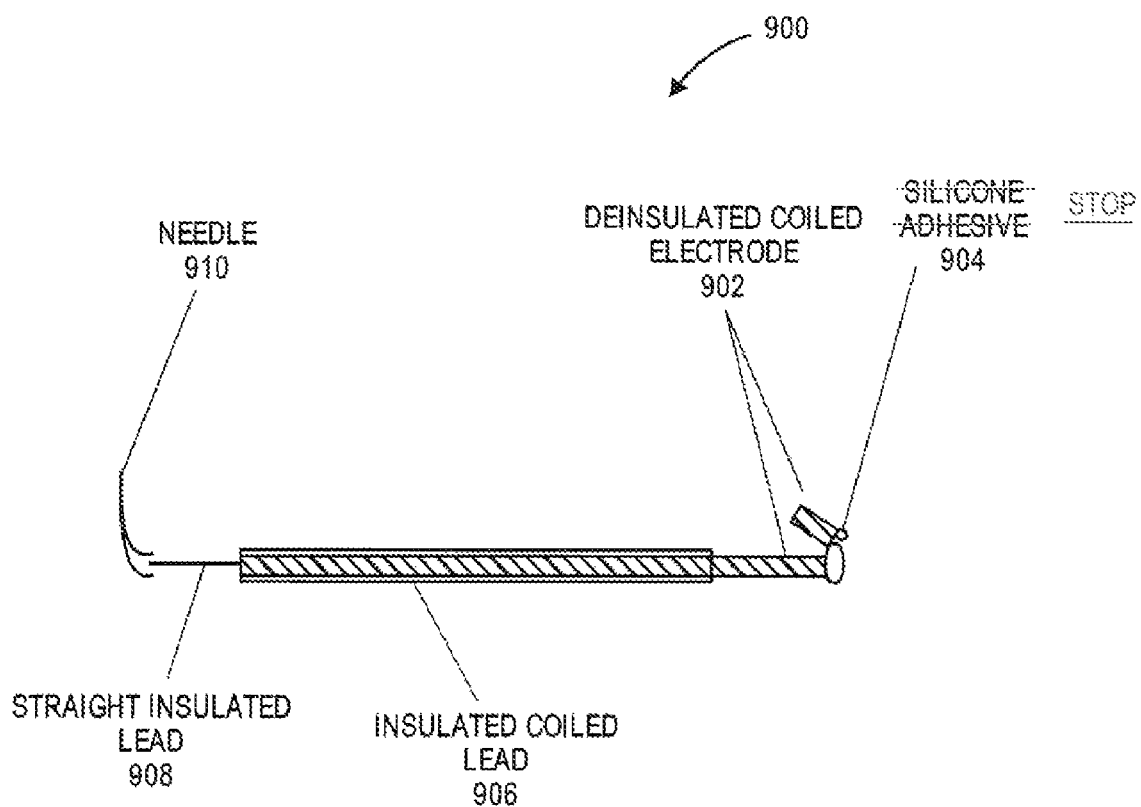
FIG. 2 shows an example of an implantable electrode.

Another example of an electrode suitable for short-term implantation is shown in FIG. 2. This electrode 900 includes five primary elements: a deinsulated stimulating segment 902, a stop 904, a length of helically coiled insulated lead 906, a length of straight insulated lead 908, and a needle 910. The stop may comprise a soft silicone plug. The electrode is inserted, needle end first, into a target site, such as diaphramatic muscle, and pulled through until the stop at the opposite end is reached. Insertion in this manner results in the deinsulated stimulating segment ending up at the surface of the target muscle at the needle entry point. The insulated lead is guided or tunneled to an appropriate exit site and the needle brought through the skin until the insulated coiled lead protrudes from the skin. The junction of the coiled to straight segment of insulated wire is secured with silicone adhesive or other suitable material to maintain the coiled configuration as it is drawn through the muscle tissue and skin interface. The coiled lead allows for tissue ingrowth at the skin exit site, thereby reducing the potential for infection entering and tracking along the lead. The needle may be a breakaway type of needle that can be used to terminate the electrode into the appropriate connector or the straight length of lead may be cut, deinsulated, and terminated into an appropriate connector. The stop may be a small amount of silicon adhesive or a piece of absorbable suture thermally locked on to the deinsulated lead.

Another example of a suitable short term intramuscular electrode was disclosed in a U.S. Provisional Patent Application filed on Feb. 5, 2007 by Ignagni, Enders, Gelbke, and Crish, entitled "Intramuscular Electrode". In one embodiment of this intramuscular electrode it comprises a single helix multistrand wire stainless steel wire insulated in fluoropolymer with a polypropylene core and barb. Embodiments of this electrode either do not have the additional skirt of the Peterson electrode, or have a skirt of a lighter gauge polypropylene skirt than that of the Peterson intramuscular electrode, so that the electrode may be withdrawn without the complication of significant ingrowth of tissue around the skirt. The lead can be implanted under video guidance or direct visualization, using the attached needle to thread it into the diaphragm. The needle and lead-in polypropylene core would be cut off after implantation. To withdraw the electrode after the intervention is completed, the electrode would be withdrawn from the opposite end by straightening the helically wound wire and pulling on the polypropylene core and wire simultaneously. This would allow for the electrode to slide out from the tissue with minimal trauma and the polypropylene core would provide the mechanical support to prevent breakage of the wire in the body.

In one embodiment, the electrodes can be implanted into target sites in the diaphragm of the patient. For example, the electrodes can be implanted into or adjacent the phrenic nerve motor points of the diaphragm (i.e., where the phrenic nerve enters the diaphragm) of the patient. The phrenic nerve motor points of the diaphragm are locations in the diaphragm that provide the greatest muscle fiber recruitment in response to an applied stimulation.

Respiratory Support System Variations and Operating Modes

Figure 3:
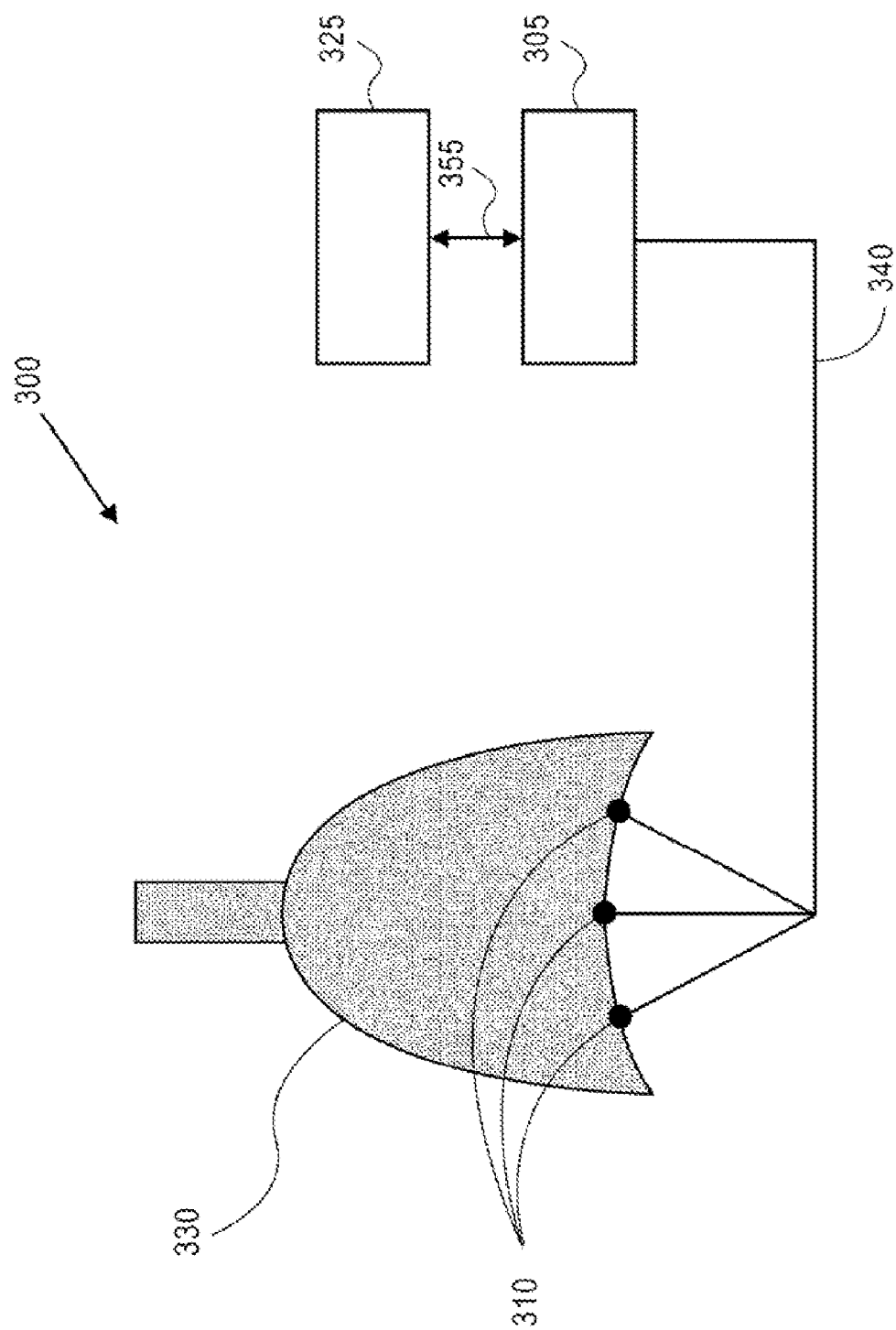
FIG. 3 is a diagram illustrating a respiratory support system (system 1) including an external stimulator.

FIG. 3 is a diagram illustrating a respiratory support system (System 1) including an external stimulator but without a PPMV. FIG. 3 is a diagram illustrating an example system 300 for assisting breathing in a patient, the patient's lungs represented as 330. Generally, the system 300 may include a stimulator 305 and one or more implantable electrodes 310 operably connected to the stimulator 305. The stimulator 305 may be configured to emit a stimulatory signal that is communicated to the implantable electrodes 310 through an operable connection 335. The stimulatory signal may be of a variety of types. Example stimulatory signals may include electrical, magnetic, and other signals.

Figure 4:
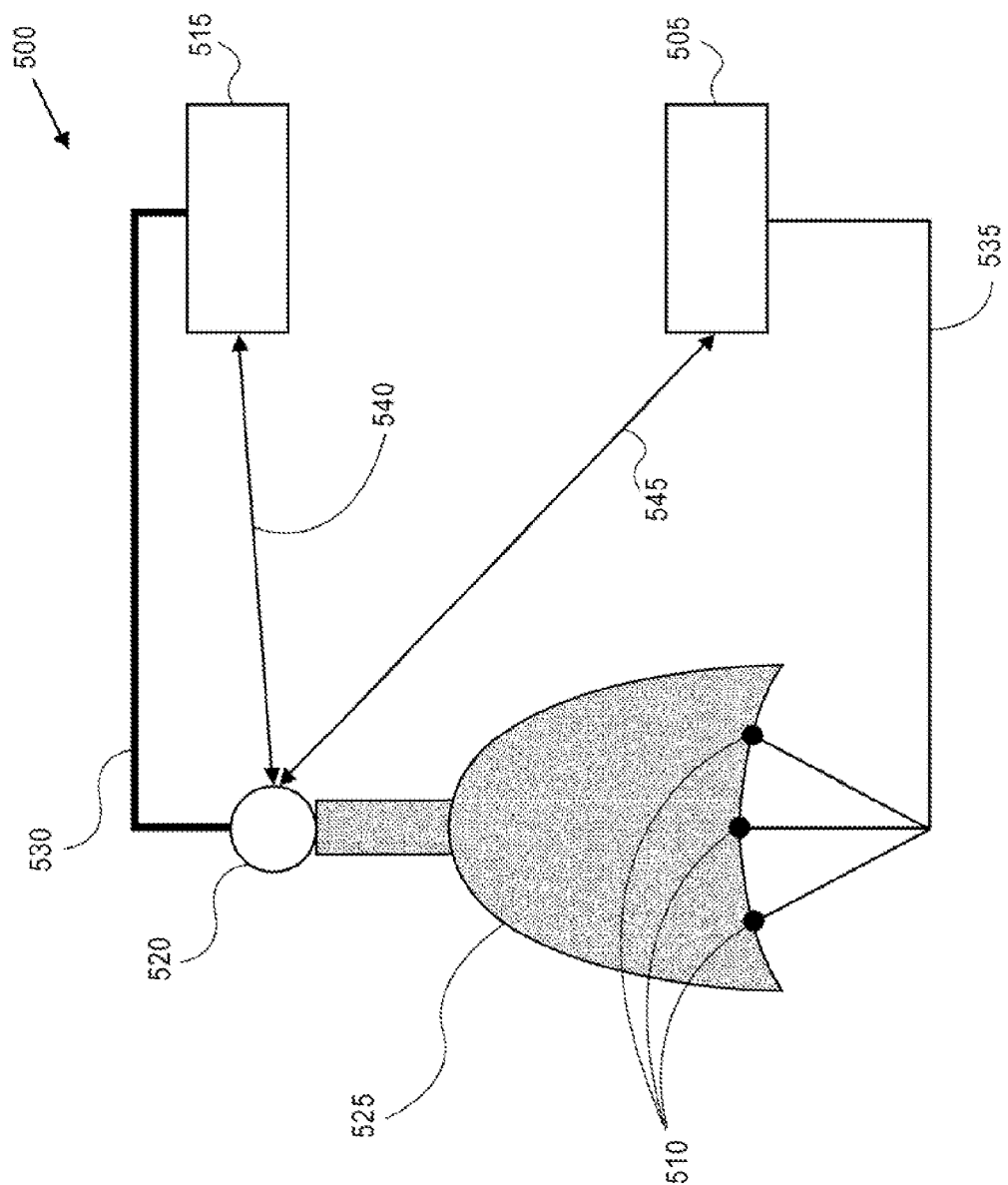
FIG. 4 is a diagram illustrating a respiratory support system (system 2) including an external stimulator and a PPMV, with an optional air flow sensor (breathing monitor) from the PPMV operably connected to both the PPMV and the external stimulator, but without a direct operable connection between the PPMV and the external stimulator.

FIG. 4 is a diagram illustrating a respiratory support system (System 2) including an external stimulator and a PPMV, with an optional air flow sensor (breathing monitor) from the PPMV operably connected to both the PPMV and the external stimulator, but without a direct operable connection between the PPMV and the external stimulator. FIG. 4 is a diagram illustrating an example system 500 for assisting breathing in a patient. Generally, the system 500 may include a stimulator 505 and one or more implantable electrodes 510 operably connected to the stimulator 505. The system 500 may also include a mechanical ventilator 515. The system 500 may also include an airflow measuring instrument or flow sensor 520.

Generally, the mechanical ventilator 515 may be configured to cycle a gas into the lungs 525 of a patient. The mechanical ventilator 515 may also be configured to cycle the gas out of the lungs 525 of the patient. In one example, the gas is delivered from the mechanical ventilator 515 to the lungs 525 of the patient through a patient circuit 530. One type of patient circuit 530 may include a set of flexible tubes. Generally, one end of the patient circuit 530 may connect to the mechanical ventilator 515 and one end of the patient circuit 530 may connect to the patient through, for example, an endotracheal tube, a tracheostomy tube, a mask covering the patient's face, and the like.

The stimulator 505 may be configured to emit a stimulatory signal that is communicated to the implantable electrodes 510 through an operable connection 535. The stimulatory signal may be of a variety of types. Example stimulatory signals may include electrical, magnetic, and other signals.

An example airflow measuring instrument 520 of flow sensor may interact with the system 500 along the ventilation breathing circuit (e.g., between the mechanical ventilator 515 and the lungs 525 of the patient). The airflow measuring instrument 520 generally is capable of sensing and/or measuring inspiratory and/or expiratory air flow in the ventilatory breathing circuit or cycle (e.g., measuring air flow in the ventilatory breathing circuit). One type of airflow measuring instrument 520 may be a pneumotachometer.

The airflow measuring instrument 520 may be capable of emitting a signal or facilitating an associated or separate logic and/or software, for example, of emitting a signal related to the sensed or measured airflow. This signal may be communicated or transmitted, directly or indirectly, to the mechanical ventilator 515. This signal may be communicated, for example, via an operable connection 540 between the airflow measuring instrument 520 and the mechanical ventilator 515. The signal from the airflow measuring instrument 520 may also or alternatively be communicated or transmitted, directly or indirectly, to the stimulator 505. This signal may be communicated, for example, via an operable connection 545 between the airflow measuring instrument 520 and the stimulator 505. The signals may facilitate timing or synchronization of a ventilatory cycle with delivery of a stimulatory signal or of delivery of a stimulatory signal with a ventilatory cycle. The signals may also or alternatively facilitate adjustment or variability in one or both of the ventilatory cycle and stimulatory signal.

Figure 5:
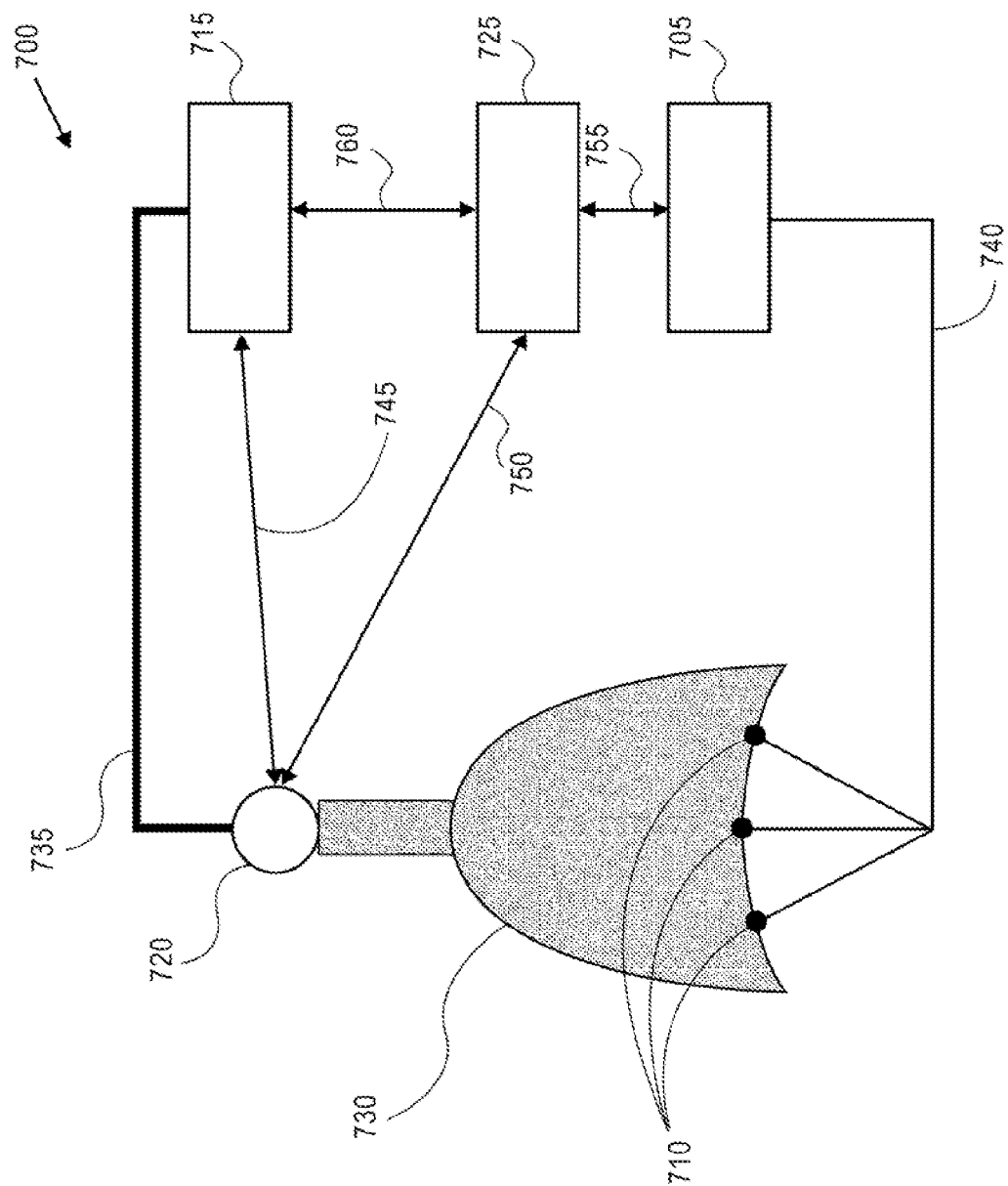
FIG. 5 is a diagram illustrating a respiratory support system (system 3) including an external stimulator and a PPMV, with an optional air flow sensor (breathing monitor) from the PPMV operably connected to both the PPMV and the external stimulator, and with an operable connection between the PPMV and the external stimulator.

FIG. 5 is a diagram illustrating a respiratory support system (System 3) including an external stimulator and a PPMV, with an optional air flow sensor (breathing monitor) from the PPMV operably connected to both the PPMV and the external stimulator, and with an operable connection between the PPMV and the external stimulator. FIG. 5 is a diagram illustrating an example system 700 for assisting breathing in a patient. Generally, the system 700 may include a stimulator 705 and one or more implantable electrodes 710 operably connected to the stimulator 705. The stimulator 705 may be configured to emit a stimulatory signal that is communicated to the implantable electrodes 710 through an operable connection 740. The system 700 may also include a mechanical ventilator 715. The mechanical ventilator 715 may be configured to cycle a gas into and/or out of the lungs 730 of a patient via a patient circuit 735. The system 700 may also include an airflow measuring instrument 720. The airflow measuring instrument 720 may be capable of sensing and/or measuring inspiratory and/or expiratory air flow in the ventilatory breathing circuit. The airflow measuring instrument 720, or an example logic associated with or separate from the airflow measuring instrument 720, may be capable of emitting a signal related to the sensed or measured airflow. This signal may be communicated or transmitted, directly or indirectly, to the mechanical ventilator 715. This signal may be communicated, for example, via an operable connection 745 between the airflow measuring instrument 720 and the mechanical ventilator 715.

The system 700 may also include a breathing sensor and control circuit 725. The breathing sensor and control circuit 725 can be configured to detect and/or determine certain breathing attributes of the patient (e.g., the inspiration phase of a breath, the duration of the inspiration phase, the exhalation phase of a breath, the duration of the exhalation phase, tidal volume, airway pressures, and/or flow rate). These breathing attributes may be communicated to the breathing sensor and control circuit 725 via, for example, an operable connection 750 between the airflow measuring instrument 720 and the breathing sensor and control circuit 725. The breathing sensor and control circuit 725 may process these signals and transmit them to the stimulator 705, for example, via an operable connection 755 between the breathing sensor and control circuit 725 and the stimulator 705. The system 700 may also include an operable connection 760 between the mechanical ventilator 715 and the breathing sensor and control circuit 725. The operable connection 760 may facilitate, for example, timing of a ventilatory cycle with delivery of a stimulatory signal.

In another example, the system 700 can include a pressure gauge (not shown) and gas meter (not shown), provided along the ventilator breathing circuit, to measure the pressure and/or gas-related parameters of the patient's breathing. Also, a physiological measurement unit can be connected to the patient to measure certain physiological parameters such as blood pressure, blood values, body temperature, etc. These measurements may be used by the system 700 to adjust or modify parameters of ventilation controlled by the mechanical ventilator 715 and or parameters of the stimulatory signal delivered by the stimulator 705.

Figure 6A:
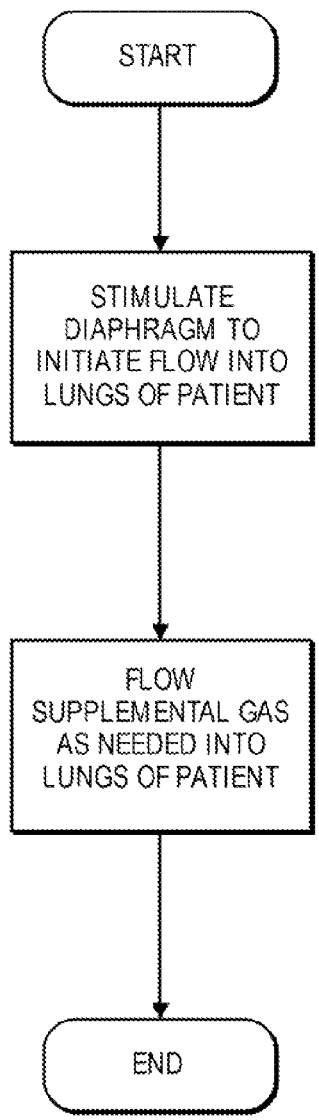
FIG. 6 is a block diagram showing three variations of respiratory support methods: (A) support with combination of PPMV and stimulator, with the stimulator initiating air flow into the lungs, (B) support with combination of PPMV and stimulator, with air flow being initiated by the PPMV, and (C) support by the stimulator alone, breath initiation either by the stimulator or by the patient, in which case the stimulator assists in completion of the breath.
Figure 6B:
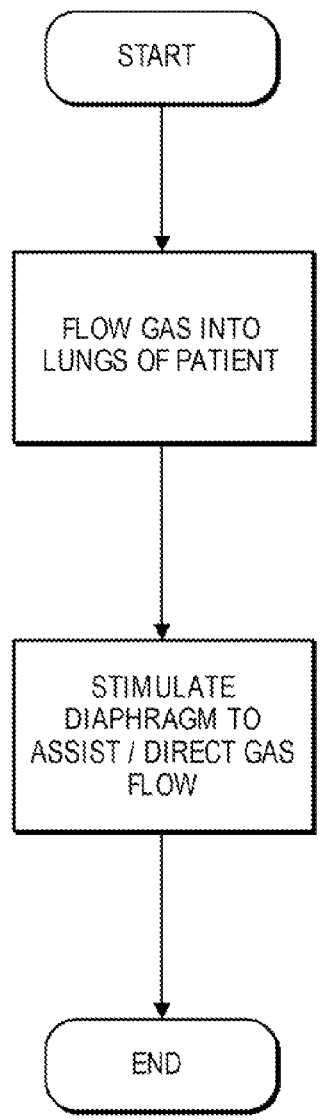
Figure 6C:
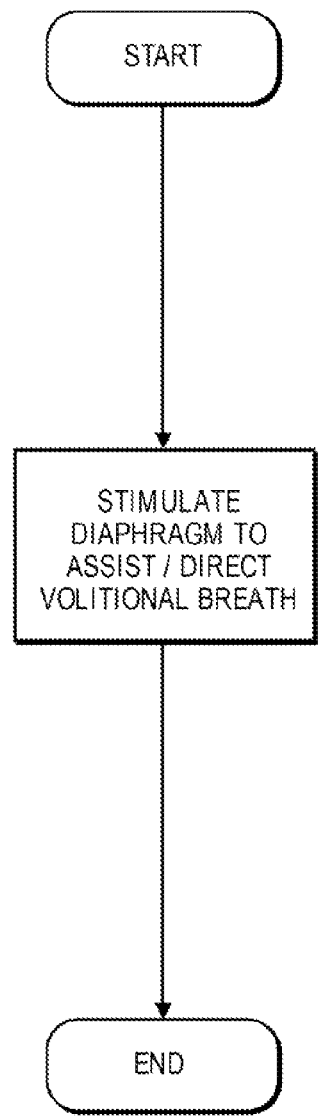

Exemplary methods may be better appreciated with reference to the flow diagram of FIG. 6 which shows three variations of respiratory support methods: (6A) support with combination of PPMV and stimulator, with the stimulator initiating air flow into the lungs, (6B) support with combination of PPMV and stimulator, with air flow being initiated by the PPMV, and (6C) support by the stimulator alone, breath initiation either by the stimulator or by the patient, in which case the stimulator assists in completion of the breath. Methods shown in 6A and 6B thus depict respiration support with the combination of electrical stimulation of diaphragm contraction that is further supported by positive airway pressure from the PPMV. By method 6A, the stimulator initiates the breath, and the PPMV provides supplemental gas under pressure to the patient as needed. In method 6B, the breath is initiated by the PPMV initiating a breath by flowing air into the lungs of the patient. In a variation of this method, the patient may initiate a breath that is detected by a gas flow detector on the PPMV, as which point the PPMV provides gas flow to support continuation of the breath. By either variation of method 6B, however, the breath is not initiated by the external stimulator, but the stimulator does activate after the breath is initiated independently of it, from which point forward the stimulator supports the breath by the diaphragm creating negative pressure within the chest. And further, by virtue of the electrode stimulation being to a specific portion of the diaphragm, the gas flow, also being supported by the PPMV is directed to a specific portion of the lung. In method 6C, the respiration is supported by the electrical stimulation of the electrodes, without participation of the PPMV. In embodiment 6C, the breath is typically initiated by the patient volitionally, and the diaphragm stimulation directs the breath by stimulating a specific portion of the diaphragm, which directs airflow toward a specific portion of the lung. In a variation of method 6C, the stimulator may initiate the breath, and then further support it as described.

Respiratory Support by Electrical Stimulation of the Diaphragm

This invention generally relates to manipulating respiratory compliance in patients in need of respiratory support, manipulating compliance in specific portions of the lung, and manipulating compliance toward specific therapeutic benefits. Compliance is manipulated or modulated through the coordinated activity of two therapeutic approaches. A first approach is by electrical stimulation of the diaphragm (diaphragm pacing), which supports respiration by way of generating negative intrathoracic pressure that expands lung volume by an external pull. Embodiments of the invention actually include therapy by this approach alone; other embodiments simultaneously include the second approach as well. The second approach is by way of a positive pressure mechanical ventilator, which supports respiration by generating a positive pressure within the lungs that expands lung volume with an outward push.

The positive pressure approach to respiratory support is quite powerful, as the mechanical ventilator can easily provide sufficient pressure to expand lung volume. This approach by itself, however has some limitation. The first limitation is that pressure, while effective in expanding lungs, can also damage lung tissue if it is too high, and used for too long a period of time. The second limitation is that positive pressure delivered by a PPMV, by itself, cannot be specifically directed to a portion of a lung. Diaphragm stimulation as a base therapeutic approach provides respiratory support that does not stress lung tissue with high internal pressure, and further, provides a capability to steer volume expansion to particular regions of lung that are in particular need of expansion, such a an atelectatic region. The combining of the two therapeutic approaches not only decreases the need for high airway pressure from the ventilator, but also adds a steering to the moderated internal pressure that the ventilator does provide. In addition to the specific therapeutic benefit of clearing an atelectatic region of a lung, for example, a number of aspects of broader hemodynamic health are provided to the patient by the generally improved respiratory compliance.

Embodiments of the described invention provide a system and methods to support the respiration of patients in a critical care setting. Such patients are typically in acute need of respiratory support, but they are anticipated to be able to recover from the need for respiratory support. These patients are thus not considered to be in need of chronic support, and accordingly, the electrodes used in this therapeutic method are implanted in the diaphragm in a manner that may be considered temporary. The invention, however, is not limited to acute patients, and may in some instances be appropriate for longer term or chronic management of respiratory disease.

The system includes an external electrical stimulator and one or more electrodes adapted to be temporarily placed in the diaphragm of a patient, the electrodes being connected to and under the control of an external stimulator. The external stimulator is configured to be able to stimulate each of the electrodes independently of each other. The method by which respiration is supported by electrical stimulation of the diaphragm includes implanting the one or more electrodes in the diaphragm of the patient, initiating a breath, and stimulating the diaphragm with the one or more electrodes during a breath to increase tidal volume and/or to decrease maximal lung pressure during the breath, thereby improving respiratory compliance. As described further below, the breath may be initiated either by the patient or by the respiratory support system. Also, as described further below, the system may further include a positive pressure mechanical ventilator. Basics of the system and method of respiratory support by diaphragmatic stimulation is provided as a stand alone therapy (i.e, in the absence of positive pressure support) is not substantially changed by the inclusion of ancillary positive pressure support, and thus will be described first as a stand alone therapy, to be followed by particulars that come with the inclusion of positive pressure support.

A breath may be understood as a breathing cycle that includes a single inspiration phase followed by a single exhalation. As provided by embodiments of the method, a breath or an attempted breath may be initiated the patient, and the patient-initiated breath is then supported at least in some portion through the cycle by diaphragm stimulation. In other embodiments of the method, the breath is initiated by the diaphragm stimulation, and then further supported at least through a portion of the cycle by further or continued diaphragm stimulation. Such an embodiment is appropriate for patients unable to initiate a breath. In this embodiment, the electrical stimulation of the diaphragm not only supports the breath, but it also determines the breathing rate. Regardless of the source of the breath initiation (patient or system), the system then supports the breath through independent stimulation of electrodes, through variation in various signal parameters as described further below, and through variable timing throughout the breath cycle, whether such stimulation is at the beginning, middle, or end of the cycle, or throughout the cycle.

Returning to the embodiment in which the breath is initiated by the patient, the initiation is sensed by the system through the electrodes themselves. In this embodiment, breath initiation, whether it would ultimately be successful without respiratory support or not, manifests as electrical activity in the diaphragmatic muscle. Such electrical activity is be captured by electrodes in the form of electromyographic data, which are processed by the microcontroller of the system (FIG. 1), and interpreted as a breath initiation attempt.

The electrodes may be implanted in the diaphragm by any of several anatomical approaches and by various surgical methods and tools. In some embodiments, the electrodes are implanted by insertion through the abdominal cavity, using either laparoscopic techniques or open surgical techniques. In other embodiments, the electrodes are implanted by insertion through the thoracic cavity, using either thoracoscopic techniques or open surgical techniques. In still other embodiments the electrodes are implanted in the diaphragm by way of insertion through natural orifices, using translumenal endoscopic techniques.

The placement of electrodes may be done under direct visualization (e.g., open surgical technique) or with video observation through a surgical camera. Location of electrode placement may be assisted with electrical stimulation mapping of the diaphragm to identify the phrenic nerve motor point or specific branches. It may be desirable to identify specific branches so as to recruit the largest anatomical surface area (e.g. anterior or posterior) portions of the diaphragm. Mapping may be done in an open procedure, thoracoscopically, or laparoscopically, or endoscopically (using a transgastric approach). Prior laparoscopic and endoscopic techniques have been described in associated patents filings (U.S. Application No. 60/597,440, U.S. Pat. No. 5,472,438, and U.S. Patent Published Application No. 2005/0107860) and are incorporated and enhanced with this invention. While direct visualization of the phrenic nerve may be accomplished with an open thoracic or thoracoscopic approach, it may be desirable, as provided by embodiments of this invention, to verify the placement location with electrical stimulation mapping of the diaphragm.

Electrodes may be implanted in the diaphragm muscle with an electrode delivery instrument; one exemplary instrument is described in U.S. Pat. No. 5,797,923. Another method, as provided by embodiments of this invention, include the use of an apparatus to puncture through the skin and provide a channel for introduction of a needle loaded with a barbed intramuscular electrode that may be inserted into the diaphragm under thoracoscopic, laparoscopic, or endoscopic visualization. If implanted during an open procedure the intramuscular electrode may be sewn into the diaphragm using a special electrode that is incorporated into this invention.

Embodiments of the method include the targeting to specific portions of the diaphragm to stimulate. Such targeting may be brought about by the selection of the diaphragm sites in which the electrodes are implanted, and it may also include the stimulation of a subset of implanted electrodes that are located in a diaphragm site of interest. A specific portion of the diaphragm may, for example, include the left hemidiphragm or the right hemidiaphragm, or any particular portion of the left or right hemidiaphragm. Stimulation of a particular portion of a diaphragm, the right or left hemidiphragm, for example, has the effect of directing or steering negative pressure to a particular portion of a patient's lungs, such as the right lung or the left lung, respectively. A particular portion of a lung may include the lower or posterior portion of the lung. In some embodiments, a particular portion of a lung may suffer from atelectasis, or collapse. In such embodiments, directing negative pressure to the collapsed portion may cause a decrease in or clearing of atelectasis.

Respiratory Support by Combination of Diaphragm Stimulation and Positive Pressure As mentioned above, some embodiments of the method include the use of a system that includes a positive pressure mechanical ventilator (PPMV) supplying positive airway pressure to the lungs in addition to the external stimulator stimulating the diaphragm to supply negative pressure external to the lungs. In these embodiments, the external stimulator generally controls the operation of the mechanical ventilator, as the two components are configured in a master-slave relationship. The positive pressure mechanical ventilator may either be invasive (e.g., endotracheal intubation or tracheostomy) or non-invasive (e.g., mask ventilation). The external stimulator may control the operation of PPMV with regard to any of the breath rate, the gas volume delivered per breath, or the airway pressure behind delivered gas. The PPMV can be set at a back-up rate so that the breathing rate is controlled by the stimulator such that either delivered gas volume or delivered airway pressure is controlled during a breath cycle. The PPMV may be controlled in such a way that maximal tidal volume is a constraint. The PPMV may also be controlled such that maximal airway pressure is a constraint.

The PPMV may be set in assist mode, where it assists within a breath cycle initiated either by the patient or by a diaphragm contraction that is stimulated by electrodes, or, alternatively the PPMV may be directly controlled by the external stimulator so that an inspiration initiated by the external stimulator triggers the PPMV to deliver supplemental gases. Further, with regard to the external stimulator, as described above, the stimulator may be configured to provide stimulation at the beginning, middle, or end of an inspiration cycle or coincidental with the entire cycle. The level of stimulation provided may be modulated during the cycle or remain constant (whether the cycle is initiated by the external stimulator or the PPMV). The stimulation may be delivered to all implanted electrodes simultaneously, to electrodes grouped by hemi-diaphragm, or to individual electrodes to preferentially contract portions of a diaphragm. The timing between stimuli delivered to specific electrodes may be sequenced so that the stimuli are delivered simultaneously, spaced throughout the stimulus cycle, or anywhere in between.

Various sequences of respiratory support with regard to the interplay of the PPMV and diaphragm stimulation are provided. For some patients in acute respiratory distress, an initial period of respiratory support that includes contributions of both a PPMV and diaphragm stimulation may be appropriate upon admission to an intensive care unit. With recovery of function, or clearing of atelectasis, for example, it may be clinically appropriate to wean the patient from the PPMV, discontinue it, and continue respiratory support with the diaphragm stimulation alone. In other cases, diaphragm stimulation may be a sufficient and appropriate mode of therapy alone, without the PPMV support. In still other cases, the condition of a patient on diaphragm stimulatory support may experience a worsening of condition, and benefit from the inclusion of positive pressure support.

Figure 7:
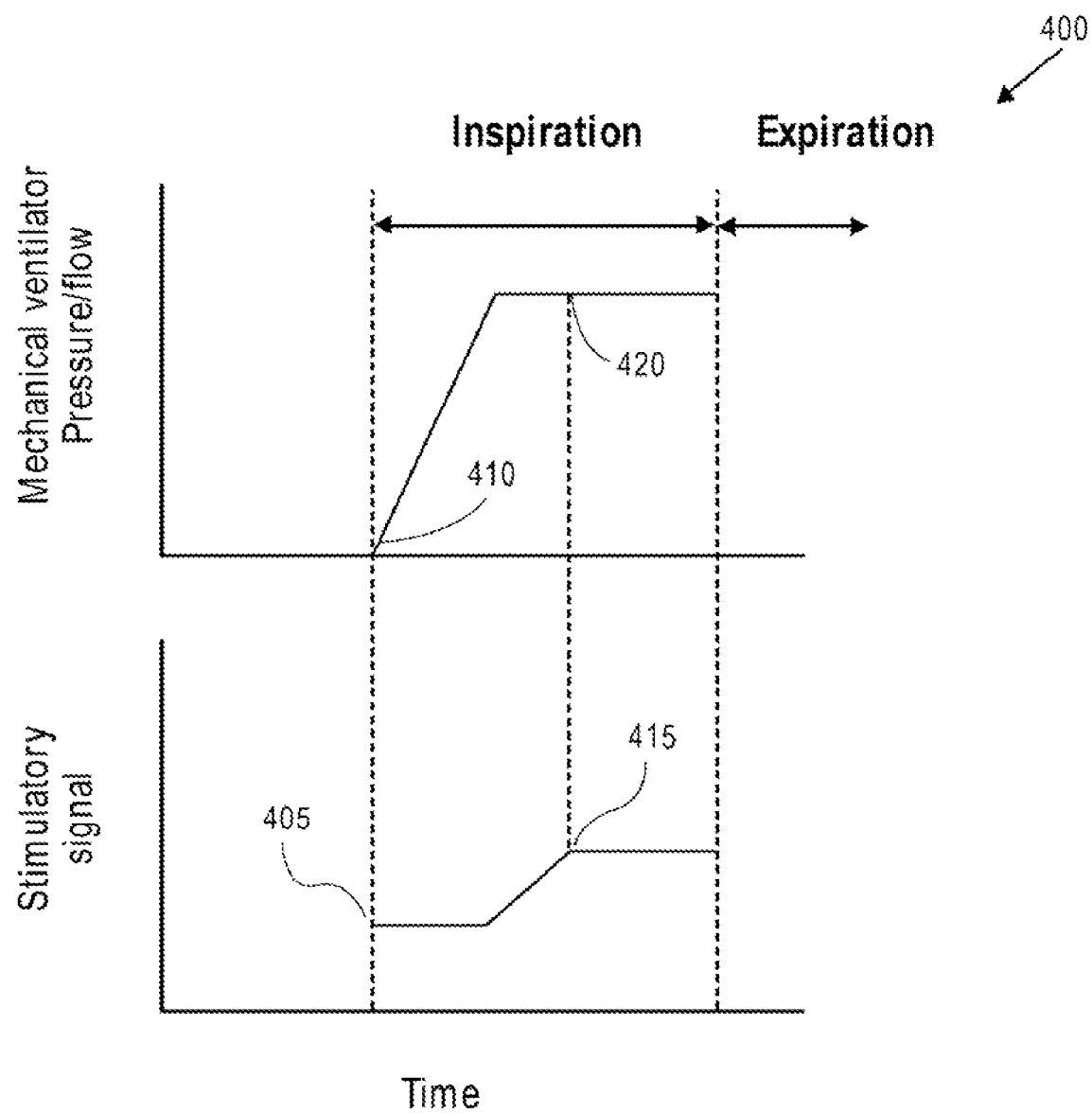
FIG. 7 is a diagram illustrating an example of coordinated timing of respiratory support as provided by a combination of an external stimulator and a positive pressure mechanical stimulator.

FIG. 7 is a diagram illustrating one example of timing between mechanical ventilation and a stimulatory signal 400. The diagram illustrates initiation of a stimulatory signal 405 with the beginning of inspiration 410 that is provided or assisted by a mechanical ventilator. The diagram also illustrates an increase in the level of the stimulatory signal 415 later in the inspiratory cycle 420. This increased stimulatory signal 415 may facilitate moving gases into the lower lobes of the lungs of the patient, for example.

The profile of generation or delivery of the stimulatory signal in relation to a ventilatory cycle, one example of which is shown in FIG. 7, may be modified for individual patients. These modifications may include, but are not limited to, the magnitude of the stimulation, the timing of the stimulation relative to the ventilatory cycle, and the rate (e.g., ramping) at which the stimulatory signal is changed during the cycle. These modifications may be implemented or facilitated by, for example, software or logic.

It will also be appreciated that stimulation of the diaphragm of the patient may not be synchronized with breathing or attempts at breathing made by the patient and, thus, can be applied during any portion of a breath or ventilatory cycle.

Respiratory Compliance

Respiratory compliance refers to the relationship between lung volume and air pressure within the lung. Optimal lung function is favored good compliance, i.e., by a high degree of responsiveness of a change in lung volume in response to change in pressure, as an increase in volume opens alveolae and creates greater lung surface area for gas exchange. Poor compliance impedes the amount of gas exchanged during a breath, which has a number of deleterious and well known consequences. Compliance involves a quality of lung tissue and resistance of airways that is associated with the state of health and integrity in a general sense, but is also a functional quality that can be manipulated or modulated by diaphragm stimulation.

Mechanical ventilation clearly provides significant benefits that follow from overcoming resistance of airways, expanding constricted alveolae that are associated with a poorly compliant lung, and generally increasing tidal volume. However, mechanical ventilation also has the potential to create high pressures that can traumatize and damage lung tissue. Patients with collapsed portions of lung, or atelectasis, have poor compliance as a consequence of the collapsed portion not expanding in response to pressure. The coordinated action of mechanical ventilation and electrical stimulation of specific diaphragm sites, as provided by the system and methods of this invention, improves compliance.

Figure 8A:
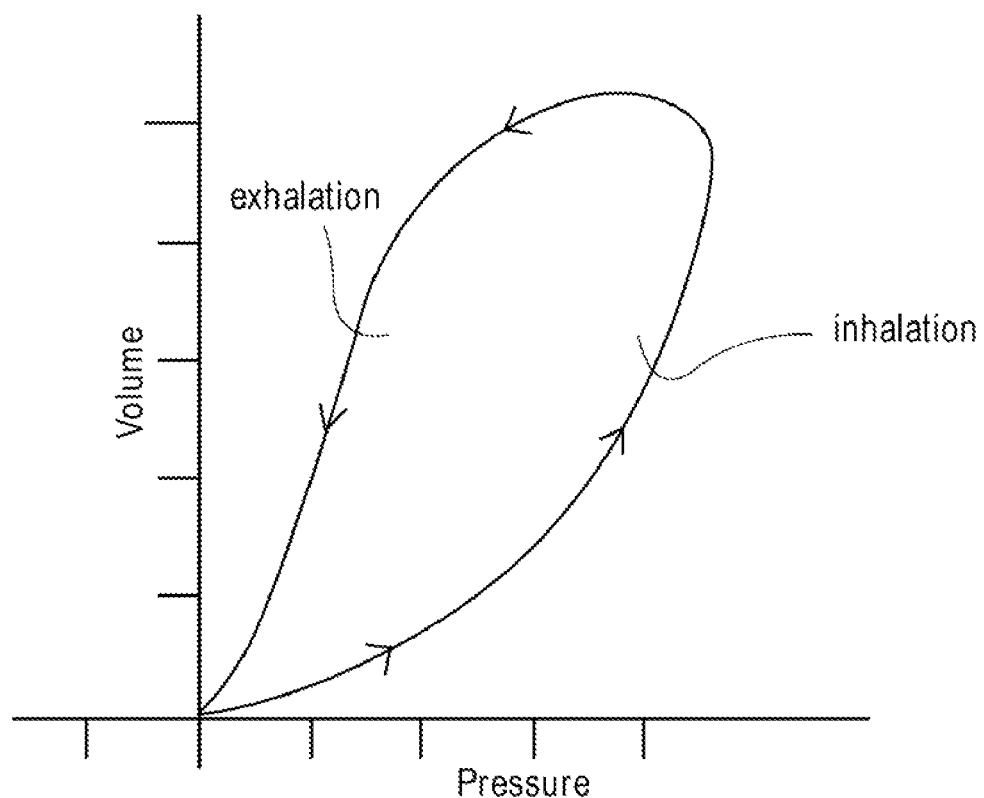
FIG. 8 is a schematic graph that compares the relationship between internal lung pressure and lung volume over the course a breathing cycle, including an inhalation and an exhalation, in a patient supported by (A) positive pressure delivered by a positive pressure mechanical ventilator (PPMV) alone, and (B) the combination of negative pressure delivered by electrically stimulated diaphragm contraction and positive pressure delivered by a PPMV.
Figure 8B:
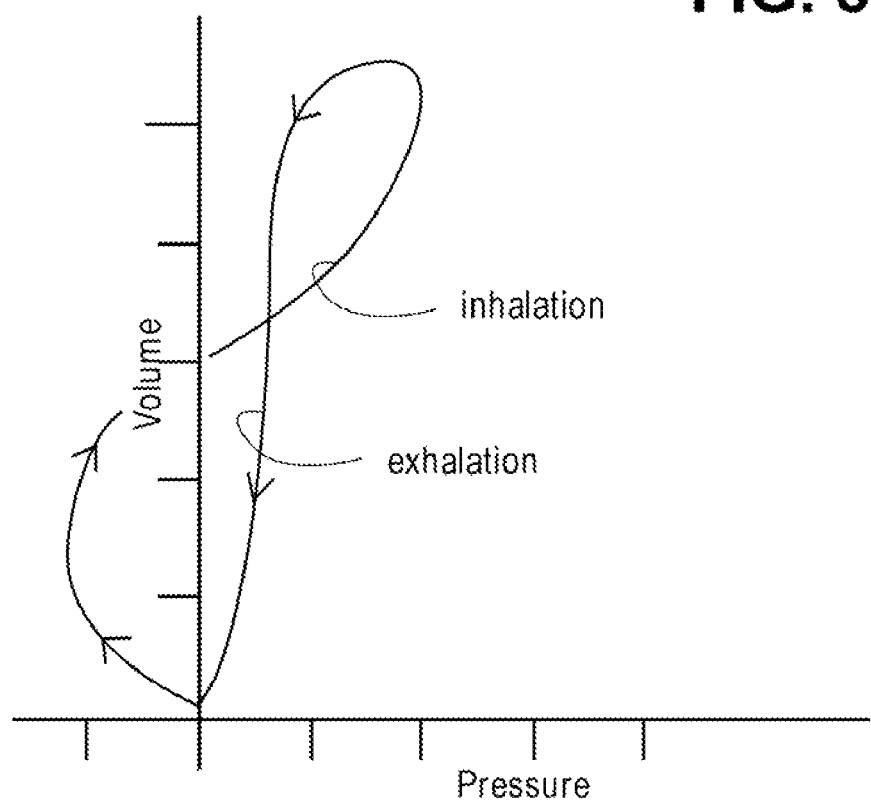

The dynamics of pressure and volume in a lung that is being supported by positive pressure mechanical ventilation (PPMV) alone and by a combination of diaphragm stimulation and PPMV is shown in an idealized schematic version in FIGS. 8A and 8B. A more detailed set off examples is described below, as depicted in FIGS. 9-12. FIG. 8A (support by PPMV only) and 8B (support by diaphragm stimulation plus PPMV) both depict lung volume as a function of air pressure within the lung through a breath cycle of a single inspiration and a single exhalation. Pressure is shown on the X-axis, and is relative to atmospheric pressure, atmospheric pressure representing zero on the X-axis. The volume is shown on the Y-axis, and is shown in terms of the increase in volume over the functional reserve capacity of the lung, i.e., the volume at the low point of a normal exhalation. The maximal volume achieved during a normal inhalation is termed the tidal volume.

The time course through the breath cycle is indicated by arrows. The graphs show the maximal volume achieved in both breaths to reach the same value. It can be seen that the breath supported by positive pressure alone (FIG. 8A) shows the intralung air pressure to increase steadily from the point of initiation of the inspiration to its conclusion, at the upper right point where the inhalation concludes. Following a different trajectory, shifted to the left, the ratio of volume to pressure falls as a smooth function back to the origin. In contrast, the time course of the volume/pressure ratio of a lung during a breath that is supported by both PPMV and diaphragm-stimulated intrathoracic negative pressure may begin with an immediate drop in pressure if the driving force from the diaphragm stimulation either precedes or is greater than the positive pressure from the PPMV. This pressure drop is due to the stimulated contraction of the diaphragm. At the same time, however, air may be flowing into the lung from the PPMV, and at a certain point that PPMV driving force from the PPMV becomes greater than that of the diaphragm stimulation the pressure reverses while the inflow of air continues. As the pressure begins to rise, the pressure crosses the baseline level, and climbs to the same peak level depicted in FIG. 8B. The pressure may drop from the peak pressure and be held at a plateau to sustain the given volume. As the pressure falls below the elastic force of the lungs and chest the volume falls steadily back to the origin during exhalation. The specific form of the curve depicted in FIG. 8B varies with timing of the stimulation, and according to other stimulatory parameters, but the point of this depiction is that under conditions of FIG. 8B, the lung is more compliant, and for a given maximal volume, the lung tissue is exposed to a significantly lower pressure.

Lung compliance may be improved, for example, by modifying diaphragm stimulation parameters to elicit a higher change in tidal volume with each inspiration or by maintaining tidal volume while reducing the delivered pressures. Compliance may be modified, preferentially, on the right or left lobes of the lungs, by separately controlling stimulation levels to the right or left hemi-diaphragm to pull gas to an otherwise unventilated region. This preferential directing of internal gas movement by way of controlling negative intrathoracic pressure can be used to reduce or clear an atelectic region. Contraction of the diaphragm also preferentially pulls the gas to the posterior or dependent lobes of the lungs and helps to prevent pneumonias.

The addition of negative pressure during the inspiration cycle may also be used to reduce the intra-thoracic pressure and thereby improve the venous return. This has the effect of increasing the cardiac stroke volume and cardiac output, thus improving the patient's hemodynamics. This should also improve any third-spacing that may be a result of PPMV. To optimize hemodynamic improvement outcome the external stimulator may be triggered by the cardiac cycle to provide optimal timing between the left ventricular filling and the contraction of the diaphragm.

Application of the method, beyond broadly improving respiratory compliance, may consequently improve a number of specific aspects of lung performance and patient health. The method may, for example, improve any of hemodynamics venous return, cardiac output, alveolar ventilation, type 1 muscle fiber condition. The method may decrease any of atlectasis, third spacing, time required for weaning from the PPMV, length of hospital stay, occurrence of pneumonia. The method may condition Type I muscle fibers, and may stimulate the conversion of Type IIb muscle fibers into Type I muscle fibers.

Some patients are at risk for the development of central hypoventilation syndrome (CHS), in such patients, the method may support a regular breathing rate during instances of hypopnea or apneas, particularly during sleep. Disturbed sleep can decrease or prevent occurrence of REM sleep, accordingly, uninterrupted sleep as supported by a regular breathing rate may increase the occurrence or duration of REM sleep. Loss of REM sleep is considered to be a causative or risk factor for intensive care unit (ICU) psychosis. Accordingly, the method may alleviate the severity or development of ICU psychosis.

What follows now (FIGS. 9-12) is a series of specific comparisons of compliance patterns that manifest under various respiratory support regimens as provided by diaphragm stimulation or PPMV support, alone and in combination. In each example an upper graph A shows a time sequence of activity of both the ventilator (above, if present) and the external electrical stimulation (below, if present), and a lower graph B shows the same data displayed as an graph of volume as a function of pressure. These examples include a pattern (FIG. 9) conventional ventilator compliance pattern without diaphragm stimulation, a compliance pattern (FIG. 10) with diaphragm stimulation only, a compliance pattern (FIG. 11) the breath is initiated by stimulation and is further supported by the PPMV, and a compliance pattern (FIG. 12) where the PPMV initiates the breath and diaphragm stimulation further supports the breath.

Figure 9A:
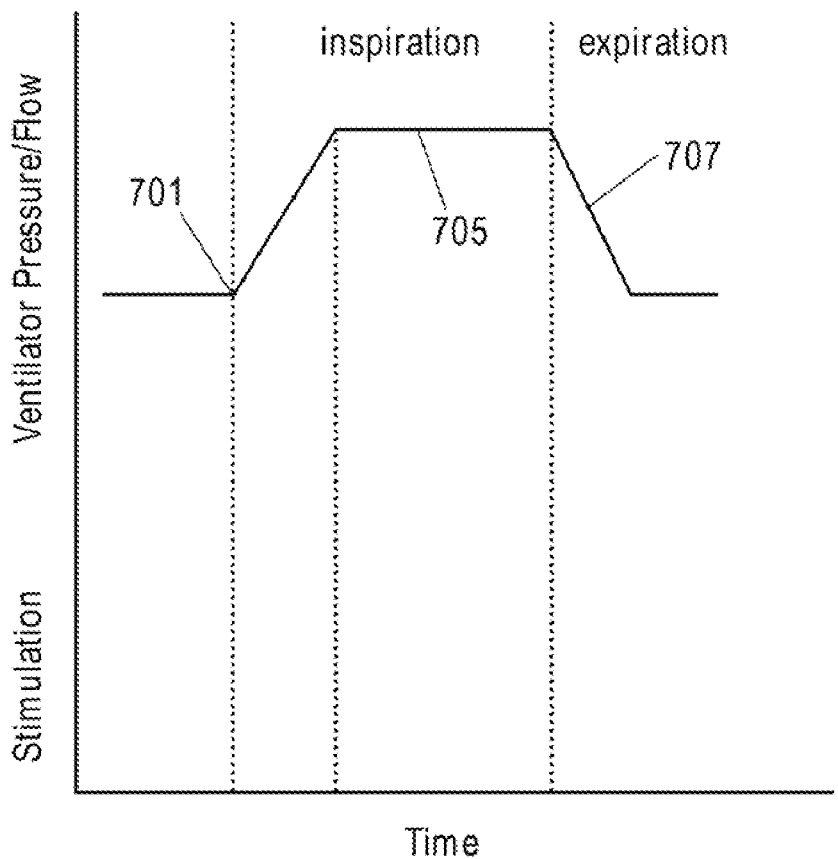
FIG. 9 shows a compliance pattern when respiration is supported by ventilation with a PPMV alone, without diaphragm stimulation.
FIG. 9B shows airway pressure with diaphragm stimulation starting approx. 1 sec into inspiration demonstrating ability to increase tidal volume and modulate airway pressure.
Figure 9B:
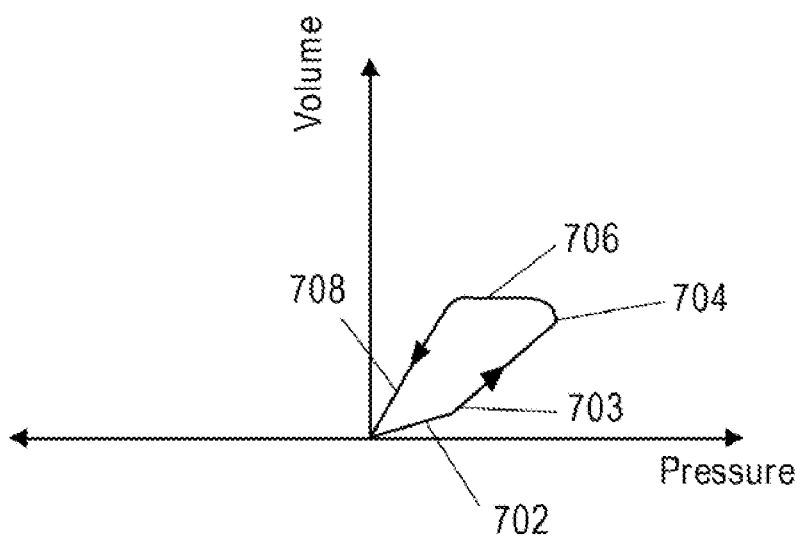

FIG. 9 shows a compliance pattern when respiration is supported by ventilation with a PPMV alone, without diaphragm stimulation. As the ventilator pressure/flow starts to increase during inspiration (701) the volume build slowly increases (702). At a given point (703) the airflow resistance decreases and the rate of volume to pressure increase becomes greater until the peak pressure (704) is reached. Once the desired volume is attained the plateau pressure is maintained (705) and the volume is held (706). Upon expiration (707), the volume is maintained (706) until the pressure falls below the elastic force of the respiratory system and an exhalation occurs (708).

Figure 10A:
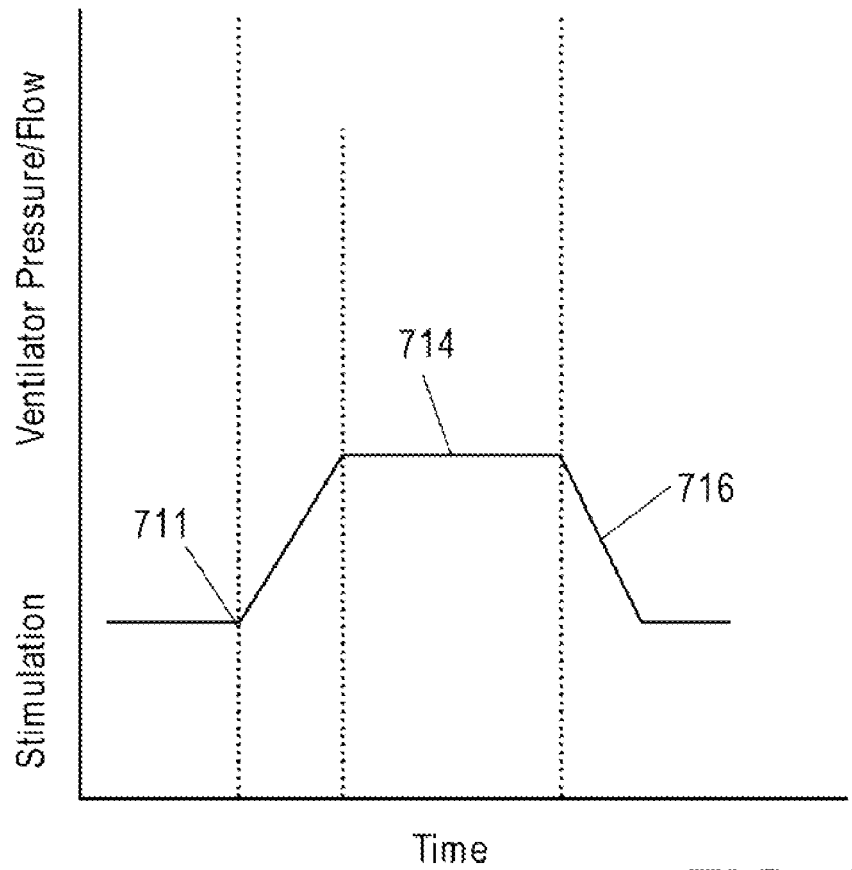
FIG. 10 shows a compliance pattern when respiration is supported by diaphragm stimulation alone (without PPMV ventilation).
Figure 10B:
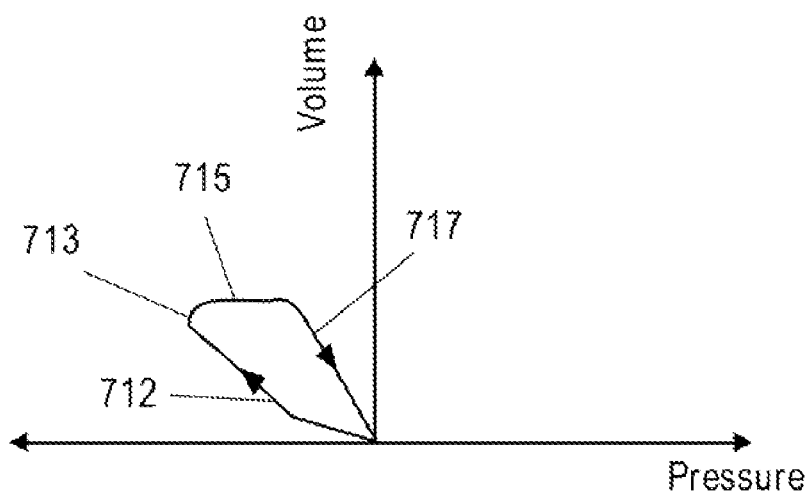

FIG. 10 shows a compliance pattern when respiration is supported by diaphragm stimulation alone (without PPMV ventilation). The stimulation is initiated (711) causing a negative pressure increase with volume drawn into the lungs (712). Once the peak stimulation level (714) is reached the peak pressure (713) is obtained and the volume held (715). Once the stimulation is turned off or ramped down (716) the inspired volume will be exhaled (717).

Figure 11A:
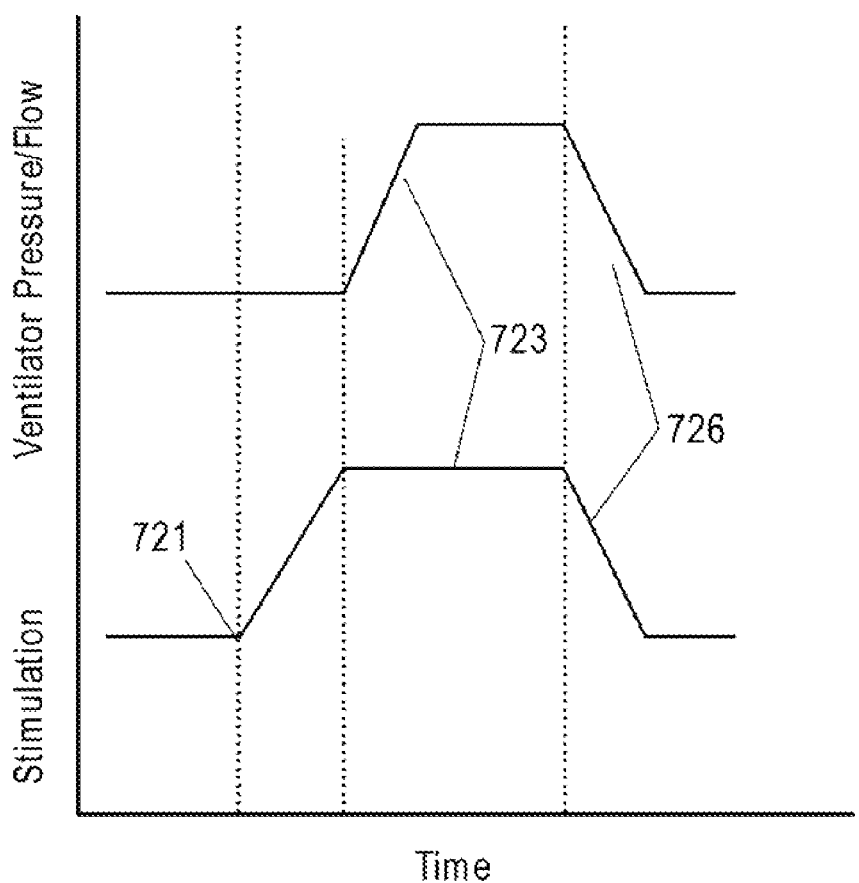
FIG. 11 shows a compliance pattern where diaphragm stimulation initiates a breath that is later supported by PPMV ventilation.
Figure 11B:
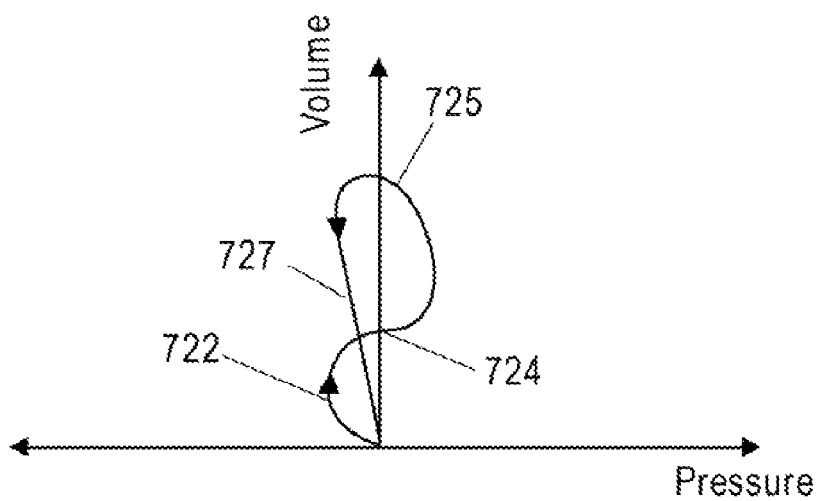

FIG. 11 shows a compliance pattern where diaphragm stimulation initiates a breath that is later supported by PPMV ventilation. The stimulation initiates the breath (721) causing a negative pressure with increasing volume (722). If the ventilator pressure exceeds the negative pressure force from the stimulation (723) the pressure curve will become positive with increasing volume (724). If the ventilator pressure is less than the negative pressure force from the stimulation (723) the pressure curve will remain negative with increasing volume (not shown). After the plateau pressure and maximum volume (725) is reached the exhalation phase may commence. The pressure is decreased until the elastic recoil of the lungs and chest causes exhalation (727). The pressure may become negative again depending on the relative force from the stimulation to the PPMV (726).

Figure 12A:
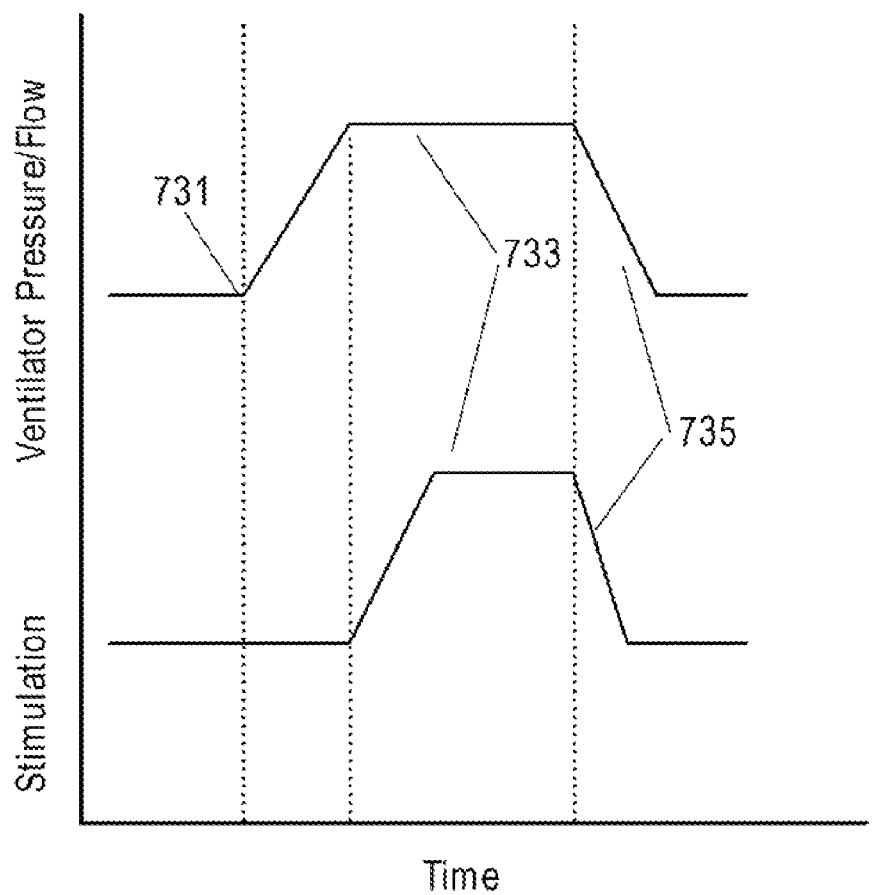
FIG. 12 shows a compliance pattern where a breath is initiated by the PPMV, and is later supported by diaphragm stimulation.
Figure 12B:
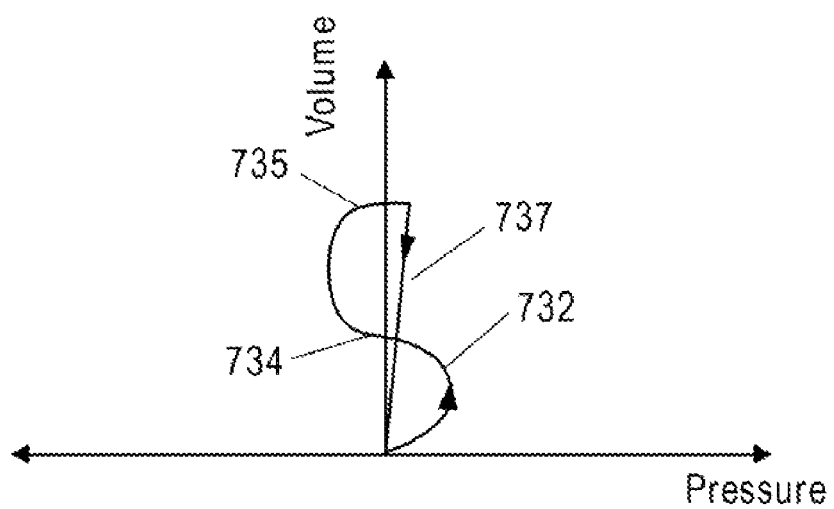

FIG. 12 shows a compliance pattern where a breath is initiated by the PPMV, and is later supported by diaphragm stimulation. The PPMV initiates the breath (731) causing a positive pressure with increasing volume (732). If the ventilator pressure is less than the negative pressure force from the stimulation (733) the pressure curve will become negative with increasing volume (734). If the ventilator pressure exceeds the negative pressure force from the stimulation (733) the pressure curve will remain positive with increasing volume (not shown). After the plateau pressure and maximum volume (735) is reached the exhalation phase may commence. The pressure is decreased until the elastic recoil of the lungs and chest causes exhalation (737). The pressure may become positive again depending on the relative force from the stimulation to the PPMV (736).

EXAMPLES OF APPLYING THE INVENTION

Example 1

Figure 13C:
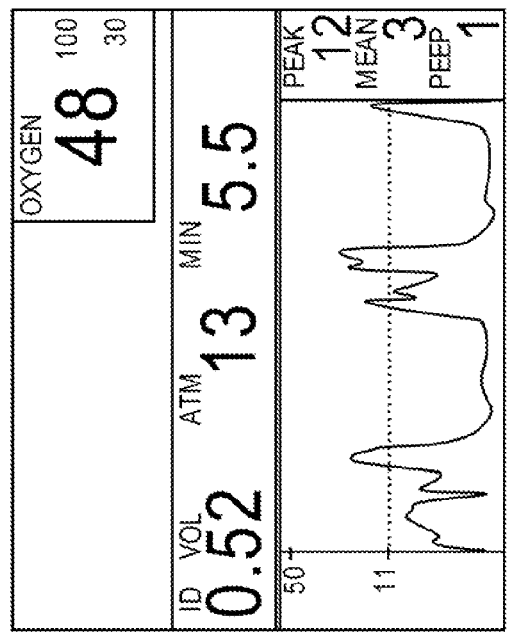
FIGS. 13A-13D provides views of airway pressure waveforms on positive pressure mechanical ventilator monitor under various conditions.
Figure 13D:
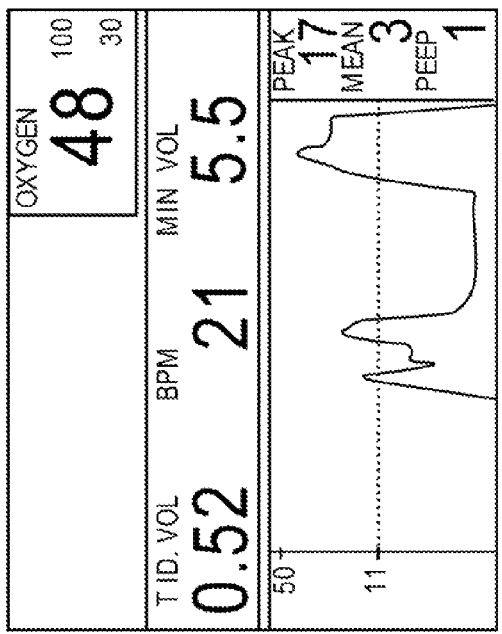
Figure 13A:
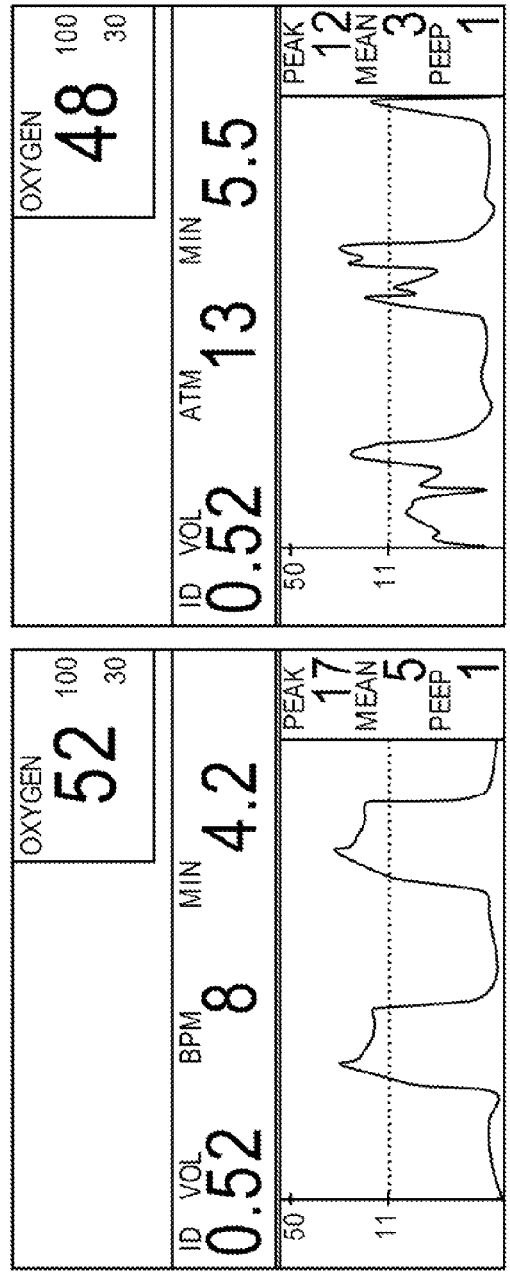

Interaction of Respiratory Support by Positive Pressure Ventilation and Negative Intrathoracic Pressure by Diaphragm Stimulation FIGS. 13A-13D show screenshots of patient data collected from a study in which positive pressure ventilation and diaphragm stimulation were variously applied. FIG. 13A (bottom left) shows a normal airway pressure waveform with ventilator support only, without diaphragm stimulation. These data show the typical increase in airway pressure until the desired tidal volume ($V_T$=0.52 liters) is achieved. A peak airway pressure ($P_{PEAK}$) of 17 cm $H_2O$ and mean airway pressure ($P_M$) of 5 cm $H_2O$ is reached under the ventilator only conditions. The minute ventilation of 4.2 liters/minute is displayed for the given $V_T$ and the measured respiratory rate (RR=8 breaths per minute) with is calculated as MV=$V_T$*RR.

Figure 13B:
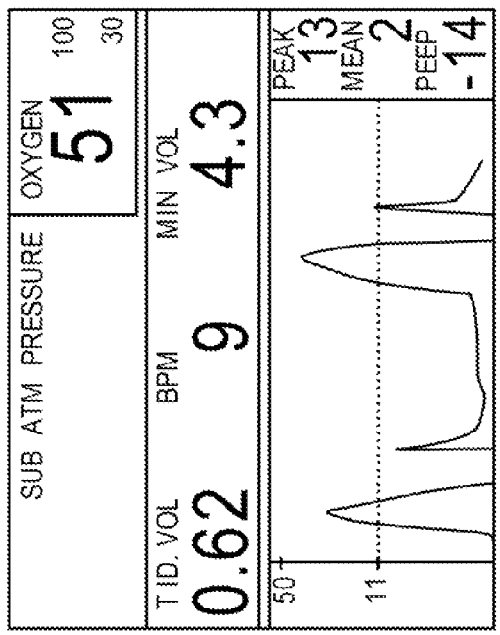

FIG. 13B (bottom right) shows airway pressure with diaphragm stimulation starting approximately 1 sec into inspiration, thus demonstrating ability to increase tidal volume and modulate airway pressure. In a "failure to oxygenate" patient the airway pressures and tidal volumes would be specifically controlled to recruit collapsed lung units (e.g. decrease atelectasis). These data demonstrate the ability to increase $V_T$ (=0.62 liters) while decreasing the airway pressures ($P_{PEAK}$=13, $P_M$=2) as compared to the ventilatory only readings. Normally, a clinician would increase the airway pressures and tidal volume to recruit collapsed lung units. By adding in the diaphragm stimulation at appropriate time during the ventilatory cycle, the peak airway pressure needed to overcome any large airway resistances may be applied and the plateau pressure ($P_{PLAT}$) reduced or eliminated thus avoiding overdistension of the lungs. In the displayed data, a stimulation pulse of 25 mA/100 µs was used to recruit diaphragm muscle contraction at a maximal level.

FIG. 13C (top left) shows airway pressure with diaphragm stimulation started near the beginning of inspiration and lasting for approximately. 1 sec, thus demonstrating ability to reduce airway pressure and maintain tidal volume. For these data, a lower level of stimulation was used, 10 mA/100 is pulse, to reduce airway pressures ($P_{PEAK}$=12 cm $H_2O$, $P_M$=3 cm $H_2O$) while maintaining a constant tidal volume ($V_T$=0.52 liters).

FIG. 13D (top right) shows airway pressure with stimulation in first inspiration and no stimulation in second inspiration. These data demonstrate the ability to modulate the airway pressure on a breath by breath basis.

Figure 14:
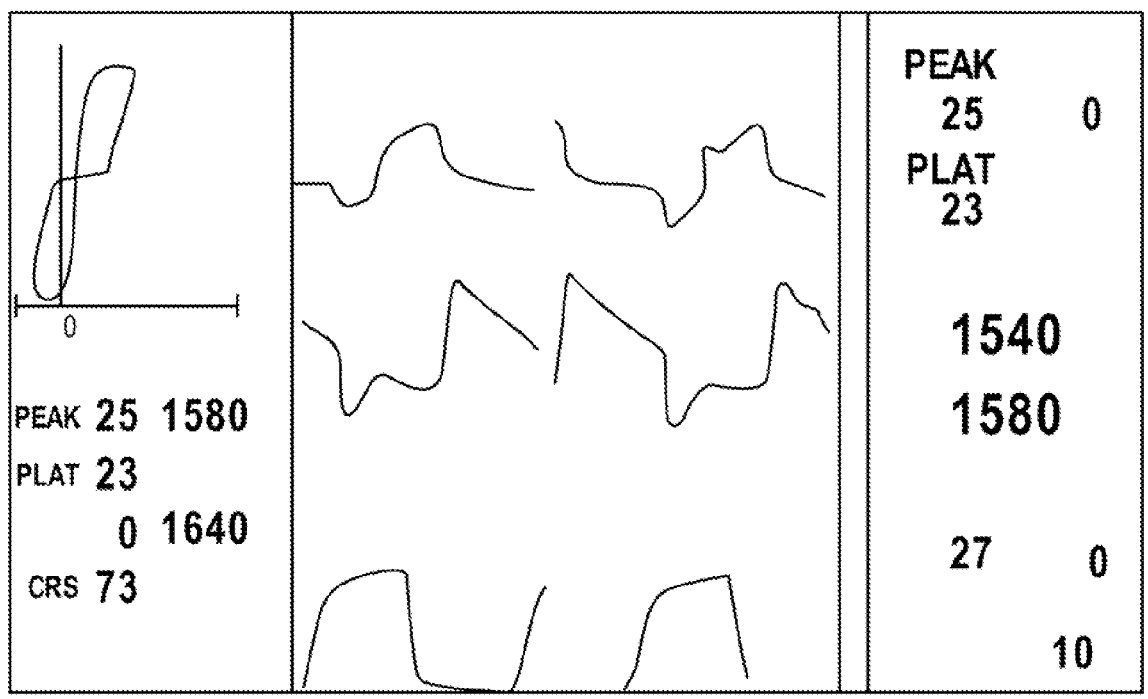
FIG. 14 shows airway compliance shift measured on positive pressure mechanical ventilator.
Figure 2:
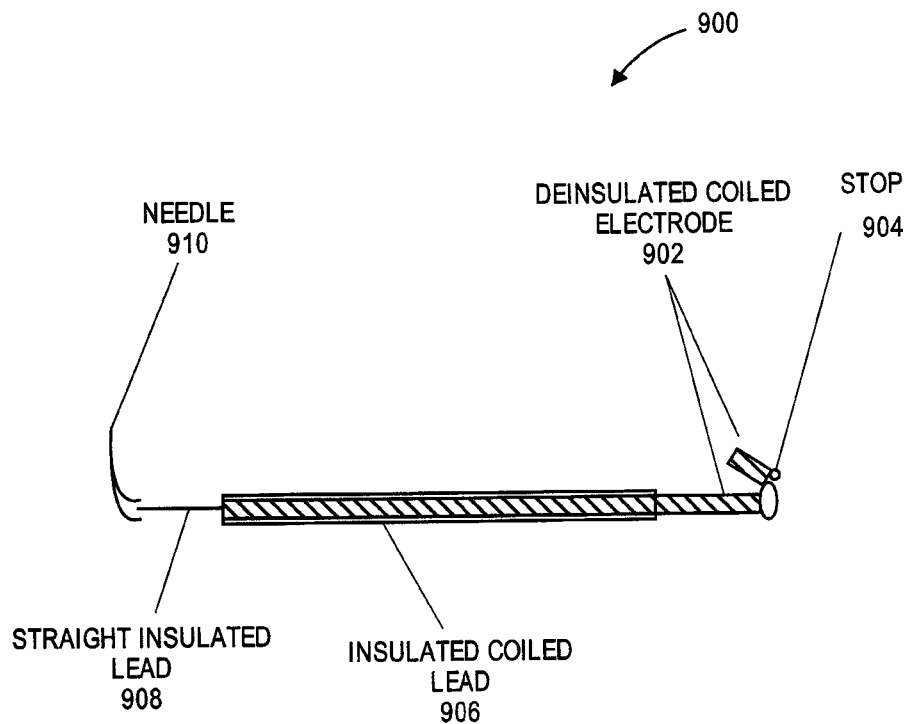

FIG. 14 demonstrates the addition of synchronous breaths to a volume ventilator and the effect upon respiratory system compliance ($C_{RS}$). The nominal settings, without diaphragm stimulation, provided $P_{PEAK}$=14 cm $H_2O$, $P_{PLAT}$=12 cm $H_2O$, $C_{RS}$=67 ml/cm $H_2O$, and $V_T$=720 ml. The addition of diaphragm stimulation early in the inspiratory cycle caused the pressure to initiate negative with increasing volume and then proceed with the continued delivery of the ventilator volume positive prior to returning to zero with completion of expiration, as shown in the pressure-volume curve in the upper left portion of the figure. The resultant tidal volume was the "stacked" volumes from the diaphragm and the ventilator, $V_T$=1,580 ml. Because of the high volume delivered the pressures increased ($P_{PEAK}$=25 cm $H_2O$, $P_{PLAT}$=23 cm $H_2O$). The respiratory system compliance also increased with the corresponding increase in volume and pressure ($C_{RS}$=73 ml/cm $H_2O$).

Example 2

Application of Diaphragm Pacing to Treatment of ALS Patients

Amyotrophic lateral sclerosis (ALS, Lou Gehrig's Disease) is a condition leading to fatal motor neuron degeneration. Muscular weakness typically progresses at the rate of 1.8% to 3.5% per month. When the muscle deterioration reaches the diaphragm, the patient develops hypercarbic respiratory failure, leading to death. ALS patients may experience different rates of decline in their left and right hemidiaphragms.

A mechanical ventilator (also known as positive pressure mechanical ventilator or PPMV) can be used to maintain breathing in ALS patients in an invasive (with tracheostomy) or non-invasive (with mask or nasal cannula) manner, but there are certain negative aspects to mechanical ventilation. In addition to the significant costs of ventilators, ventilated patients suffer from speech difficulty, further reduced mobility, and create a heightened burden on caregivers. More significant are the deleterious physiologic effects of positive pressure ventilation, such as a decrease in remaining diaphragm strength due to atrophy of the muscle and to conversion of Type I fibers to Type IIb. The increased thoracic pressure caused by PPMV can lead to decreased cardiac output and barotrauma, with possible posterior lobe collapse, atelectasis and/or pneumonia. Further, many ALS patients do not tolerate non-invasive PPMV, due to the bulbar symptoms of the disease, and most of them do not accept invasive PPMV.

Functional electrical stimulation of the diaphragm, with or without PPMV, can pace the diaphragm to maintain diaphragm function. In addition to assisting breathing by causing diaphragm contraction through direct stimulation at phrenic nerve motor points, diaphragm pacing can induce new nerve branching in the diaphragm, counteract muscle atrophy and slow the decline of forced vital capacity (FVC) in ALS patients. Diaphragm pacing can reduce patient airway pressure, increase overall ventilation, increase diaphragm strength, maintain Type 1 diaphragm muscle fibers, improve cardiac output and provide increased posterior lobe ventilation.

Twelve patients with FVC between 50-80% and >45% at the time of surgery (average 58% FVC) were enrolled in the study. Electrodes were implanted laparoscopically in the patients' two hemidiaphragms at motor points determined during an earlier mapping procedure, and stimulation was provided in 30 minute sessions three to five times per day. Stimulation was provided at 12 Hz, with the pulse width and amplitude as much as the patient could tolerate (typically around 10 ma, pulse width 150 ms) to provide the patient with 8-15 breaths per minute. Patients were permitted to increase stimulation utilization over time if desired. In addition to measuring FVC and other lung capacity parameters, diaphragm thickness was measured ultrasonically, blood gases were sampled, and patient quality of life information was surveyed.

The diaphragm pacing system used for stimulation can provide different stimulation signals to each electrode in each hemidiaphragm. Stimulation parameters can be varied by amplitude, frequency, rate, pulse width and pulse modulation. Diaphragm muscle mass increased over the course of the diaphragm pacing as shown in the Table 2 below:

TABLE 2

| Test Location | Pre-Implant (mm) | Post-implant (mm) | P-value |
|---|---|---|---|
| L @ expiration | 3.9 +/− 0.7 | 4.8 +/− 1.2 | 0.02 |
| R @ expiration | 3.8 +/− 0.9 | 4.7 +/− 1.1 | 0.01 |

In addition, improved diaphragm movement was observed under fluoroscopy. Diaphragm contraction increased with stimulation compared to volitional movement an average of 1.5 cm per hemidiaphragm. Furthermore, the decline of FVC decreased from 2.8% to 1.0%, thereby delaying the time when the ALS patient would need to begin using mechanical ventilation.

The diaphragm stimulation in ALS patients was also shown to sustain the respiratory function of the patients as measured by standard means using the revised ALS Functional Rating Scale (ALSFRSr). In the set of patients studied the overall functional rating score decreased at a rate of 0.7 points per month while the respiratory subscore remained constant. These same patients showed a decline in physical and emotional domains of a standard quality of life instrument, the SF-36 prior to treatment and demonstrated an improving trend in scores post treatment.

Diaphragm pacing can also be used together with non-invasive mechanical ventilation in the ALS patients to decrease peak airway pressure and increase tidal volume, making the intervention of non-invasive PPMV tolerated by a greater portion of ALS patients. This intervention would also increase respiratory compliance, reduce atelectatic lung regions and thereby reduce the risks of acute respiratory failures.

Example 3

Respiratory Support for a Heavily Sedated ICU Patient

For a heavily sedated ICU patient with no respiratory drive a volume ventilator mode may be used to provide ventilatory needs. The diaphragm pacing may be used to assist in this case to (1) preferentially ventilate the dependent portions of the lungs to avoid atelectasis, (2) reduce the applied pressures, and (3) reduce the work of breathing by increasing the respiratory system compliance, as outlined below.
  1. To preferentially ventilate the dependent portions of the lungs the stimulation may be applied after the volume delivery commences (after the peak pressure but prior to completion of the positive gas flow) to draw the delivered air to the posterior lobes. With a heavily sedated patient higher stimulus parameters may be used, if needed, as any discomfort from the stimulus would not be felt by the patient.
  2. To reduce the applied pressures the stimulation may initiate coincidental to the ventilated breath to reduce peak airway pressure or subsequent to the peak to reduce the plateau pressure. The stimulation could be ramped on at a rate (over the gas delivery) to avoid an in-rush of negative inspiratory force and stacked breaths.
  3. The stimulation may be applied at a lower level (e.g. amplitude of 10 mA as opposed to 25 mA) at the beginning of the ventilatory cycle to reduce initial peak pressures or throughout the gas delivery to reduce peak and plateau pressure while maintaining the tidal volume (as in FIG. 3C) thus increasing the respiratory system compliance.

For a patient that is not heavily sedated and/or is appropriate for pressure support ventilation the stimulation can be used to provide the primary ventilatory support with the ventilator as a backup. The diaphragm stimulation would be set to obtain the desired volume at stimulation values that the patient could tolerate. For a typical patient the stimulus may be set in a range of 10-25 mA at a pulse duration of 100 μs and pulse frequency of 10-15 Hz. If adequate ventilation is obtained the ventilator would be set to provide only backup to the stimulated support. If adequate volumes are not obtained the ventilator pressure would be increased until adequate volumes are obtained. This support could be done with endotracheal or mask ventilation.

All publications, patents, and patent applications cited herein are hereby incorporated by reference in their entirety for all purposes to the same extent as if each individual publication, patent, or patent application were specifically and individually indicated to be so incorporated by reference.

Other variations of method and aspects of the system can be employed to achieve the objectives of the invention without departing from the scope of the invention, as will be appreciated by those skilled in the art. While various embodiments of the present invention have been shown and described herein, it will be obvious to those skilled in the art that such embodiments are provided by way of example only. The invention generally relates to manipulating respiratory compliance toward therapeutic ends, and in describing the invention, the application has offered some theoretical explanation as to how these ends may be achieved. It should be understood, however, that such theories and interpretation do not bind or limit the claims with regard to the therapeutic benefits brought about by the practice of the invention. Numerous variations, changes, and substitutions will occur to those skilled in the art without departing from the invention. It should be thusly and further understood that various alternatives to the embodiments of the invention described herein that may be employed in practicing the present invention are considered equivalents to the invention, and that it is intended that the scope of the invention includes such equivalents.

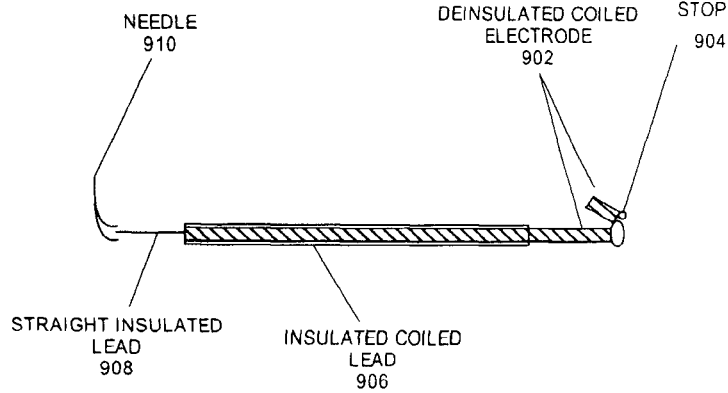

We claim:
1. An electrode suitable for temporary placement in diaphragm tissue comprising:
   a needle at a first end,
   a central portion comprising a straight insulated lead, a helically wound insulated lead portion, and a deinsulated coiled portion, and
   a deinsulated barb and a stop at a second end adjacent to the deinsulated coiled portion, wherein the stop is configured to hold the deinsulated barb and the deinsulated coiled portion at the surface of the diaphragm.

2. The electrode of claim 1 wherein the stop comprises soft silicone.

3. The electrode of claim 1 wherein the stop comprises an absorbable suture material thermally bonded to the deinsulated coiled portion.

4. The electrode of claim 1 wherein the needle is a breakaway needle.

5. The electrode of claim 1 wherein the straight insulated lead and the helically wound insulated lead are joined at a junction, the electrode further comprising a bonding material disposed at the junction to form a bond configured to prevent the helically wound lead from unwinding.

6. A method of inserting an electrode suitable for temporary placement in a patient's diaphragm, the electrode comprising a needle at a first end, a central portion comprising a straight insulated lead, a helically wound insulated lead portion, and a deinsulated coiled portion, and a deinsulated barb and a stop at a second end, the method comprising:
  inserting the electrode into the diaphragm surface by the first end comprising the needle
  pulling the electrode through the diaphragm until the second end comprising the stop is at the diaphragm surface; and
  connecting the first end to an external electrical stimulator.

7. The method of claim 6 wherein the electrode stop comprises soft silicone.

8. The method of claim 6 wherein the electrode stop comprises an absorbable suture material thermally bonded to the deinsulated coiled portion.

9. The method of claim 6 wherein the electrode needle is a break-away needle.

10. The method of claim 6 wherein the electrode's straight insulated lead and the helically wound insulated lead are joined at a junction, the electrode further comprising a bonding material disposed at the junction to form a bond configured to prevent the helically wound lead from unwinding.

11. The method of claim 6, further comprising coupling the first end of the electrode to an electrical connector.

12. The method of claim 6, further comprising pulling the needle thorough the patient's skin until the insulated helically wound lead protrudes from the skin.

13. The method of claim 6, further comprising securing the junction of the helically wound insulated lead portion to the straight insulated lead to the patient to maintain the coiled configuration of the electrode.

14. The method of claim 6, wherein the step of connecting the first end to an external electrical stimulator comprises breaking away the needle from the first end and connecting the first end to the electrical stimulator.

15. The method of claim 6, wherein the step of connecting the first end to an external electrical stimulator comprises cutting the straight insulated lead and de-insulating at least a portion of the straight insulated lead and connecting the de-insulated portion to the electrical stimulator.

16. An electrode suitable for temporary placement in diaphragm tissue comprising:
  a needle at a first end,
  a central portion comprising a straight insulated lead adjacent to the needle, a helically wound insulated lead portion, and a deinsulated coiled portion adjacent to the second end, and
  a deinsulated barb at the second end and a stop formed between the deinsulated barb and the deinsulated coiled portion, wherein the stop is configured to hold the deinsulated barb and the deinsulated coiled portion at the surface of the diaphragm.

* * * * *

UNITED STATES PATENT AND TRADEMARK OFFICE
CERTIFICATE OF CORRECTION

| | | |
|---|---|---|
| PATENT NO. | : 7,962,215 B2 | Page 1 of 3 |
| APPLICATION NO. | : 11/716459 | |
| DATED | : June 14, 2011 | |
| INVENTOR(S) | : Anthony R. Ignagni and Raymond P. Onders | |

It is certified that error appears in the above-identified patent and that said Letters Patent is hereby corrected as shown below:

On the Title Page; Replace FIG. 2 with the attached.

Drawing Sheet 2 of 14; Replace FIG. 2 with the attached.

Column 1, line 58; after "external", delete "simulator." and insert --stimulator.--.

Column 2, line 2; after "the left", delete "hemidiphragm" and insert --hemidiaphragm--.

Column 3, line 57; after "implanted or", delete "a".

Column 7, line 57; after "by Ignagni,", delete "Enders" and insert --Onders--.

Column 11, line 65; after "may be initiated", insert --by--.

Column 14, line 64; after "detailed set", delete "off" and insert --of--.

Column 16, line 27; after "data displayed as", delete "an" and insert --a--.

Column 22, line 7; after "needle", delete "thorough" and insert --through--.

Signed and Sealed this
Twenty-second Day of May, 2012

David J. Kappos
*Director of the United States Patent and Trademark Office*

(12) United States Patent
Ignagni et al.

(10) Patent No.: US 7,962,215 B2
(45) Date of Patent: Jun. 14, 2011

(54) VENTILATORY ASSIST SYSTEM AND METHODS TO IMPROVE RESPIRATORY FUNCTION

(75) Inventors: Anthony R. Ignagni, Oberlin, OH (US); Raymond P. Onders, Shaker Heights, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 700 days.

(21) Appl. No.: 11/716,459

(22) Filed: Mar. 9, 2007

(65) Prior Publication Data
US 2007/0265611 A1 Nov. 15, 2007

Related U.S. Application Data

(63) Continuation-in-part of application No. 10/897,685, filed on Jul. 23, 2004, now Pat. No. 7,840,270.

(60) Provisional application No. 60/767,201, filed on Mar. 9, 2006, provisional application No. 60/861,568, filed on Nov. 28, 2006, provisional application No. 60/872,265, filed on Dec. 1, 2006.

(51) Int. Cl.
*A61N 1/36* (2006.01)

(52) U.S. Cl. ...................................................... 607/42

(58) Field of Classification Search .................. 607/116
See application file for complete search history.

(56) References Cited

U.S. PATENT DOCUMENTS

| 1,693,734 | A | 12/1928 | Waggoner |
| 2,532,788 | A | 12/1950 | Sarnoff |
| 2,664,880 | A | 1/1954 | Wales, Jr. |
| 4,699,875 | A | 10/1987 | Appel |
| 4,827,935 | A | 5/1989 | Geddes et al. |
| 4,830,008 | A | 5/1989 | Meer |
| 4,989,617 | A | 2/1991 | Memberg et al. |

(Continued)

FOREIGN PATENT DOCUMENTS

EP 996482 A1 5/2000

(Continued)

OTHER PUBLICATIONS

Onders et al., U.S. Appl. No. 12/122,482 entitled "Devices and methods for assessing motor point electromyogram as a biomarker." filed May 16, 2008.

(Continued)

*Primary Examiner* — Carl H Layno
*Assistant Examiner* — Jeremiah T Kimball
(74) *Attorney, Agent, or Firm* — Shay Glenn LLP

(57) ABSTRACT

Systems and methods are provided to improve respiratory function. Systems include an external electrical stimulator coupled to electrodes that stimulates diaphragm contraction and may optionally include a positive pressure mechanical ventilator. The system further includes an electrode suitable for temporary implantation. Electrical stimulation is provided to specific portions of the diaphragm, such as one hemidiaphragm preferentially over another. By preferentially contracting one hemidiaphragm, a specific portion of a lung may be expanded, such as a posterior portion. By the provision of the negative intrathoracic pressure from diaphragm contraction, greater expansion of specific portion of lung is achieved in relationship to air pressure within the lung, thereby improving compliance. Supplementation of stimulated diaphragm contraction with positive pressure driven air flow from a PPMV directs the air flow to specific portions of the lung. Such portion may include a posterior portion of a lung, and may cause a clearing of atelectasis in that portion.

16 Claims, 14 Drawing Sheets